US011034925B2

(12) United States Patent
Hung et al.

(10) Patent No.: US 11,034,925 B2
(45) Date of Patent: *Jun. 15, 2021

(54) CELL CULTURE AND INVASION ASSAY METHOD AND SYSTEM

(71) Applicant: EMD Millipore Corporation, Burlington, MA (US)

(72) Inventors: Paul J. Hung, Berkeley, CA (US); Philip J. Lee, Alameda, CA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/713,117

(22) Filed: Dec. 13, 2019

(65) Prior Publication Data

US 2020/0208089 A1 Jul. 2, 2020

Related U.S. Application Data

(60) Continuation of application No. 15/459,332, filed on Mar. 15, 2017, now Pat. No. 10,526,572, which is a division of application No. 13/436,992, filed on Apr. 1, 2012, now Pat. No. 9,637,715.

(60) Provisional application No. 61/471,103, filed on Apr. 1, 2011.

(51) Int. Cl.
| | |
|---|---|
| *C12M 3/00* | (2006.01) |
| *B01L 3/00* | (2006.01) |
| *C12M 1/32* | (2006.01) |
| *C12M 3/06* | (2006.01) |
| *C12M 1/00* | (2006.01) |
| *C12M 1/12* | (2006.01) |

(52) U.S. Cl.
CPC .......... *C12M 23/12* (2013.01); *C12M 23/16* (2013.01); *C12M 25/14* (2013.01); *C12M 29/04* (2013.01); *C12M 29/10* (2013.01); *C12M 29/14* (2013.01)

(58) Field of Classification Search
CPC ....... C12M 25/04; C12M 25/02; C12M 23/16
See application file for complete search history.

(56) References Cited

U.S. PATENT DOCUMENTS

| | | | |
|---|---|---|---|
| 4,055,613 | A | 10/1977 | Kapral |
| 4,661,455 | A | 4/1987 | Hubbard |
| 4,734,373 | A | 3/1988 | Bartal |
| 4,748,124 | A | 5/1988 | Vogler |
| 5,079,168 | A | 1/1992 | Amiot |
| 5,153,131 | A | 10/1992 | Wolf et al. |
| 5,310,676 | A | 5/1994 | Johansson et al. |
| 5,330,908 | A | 7/1994 | Spaulding |
| 5,376,252 | A | 12/1994 | Ekstrom et al. |

(Continued)

FOREIGN PATENT DOCUMENTS

| | | |
|---|---|---|
| CN | 201803927 U | 4/2011 |
| DE | 19948087 A1 | 5/2001 |

(Continued)

OTHER PUBLICATIONS

Office action dated Apr. 7, 2020 in co-pending U.S. Appl. No. 15/958,480.

(Continued)

*Primary Examiner* — Nathan A Bowers
(74) *Attorney, Agent, or Firm* — Nields, Lemack & Frame, LLC

(57) ABSTRACT

Microfluidic devices, systems, and methods providing for an invasion assay using microfluidic culture systems.

20 Claims, 19 Drawing Sheets

(56) References Cited

U.S. PATENT DOCUMENTS

| | | |
|---|---|---|
| 5,416,022 A | 5/1995 | Amiot |
| 5,424,209 A | 6/1995 | Kearney |
| 5,437,998 A | 8/1995 | Schwarz et al. |
| 5,451,524 A | 9/1995 | Coble et al. |
| 5,462,874 A | 10/1995 | Wolf et al. |
| 5,565,353 A | 10/1996 | Klebe et al. |
| 5,589,112 A | 12/1996 | Spaulding |
| 5,593,814 A | 1/1997 | Matsuda et al. |
| 5,602,028 A | 2/1997 | Minchinton |
| 5,627,070 A | 5/1997 | Gruenberg |
| 5,637,469 A | 6/1997 | Wilding et al. |
| 5,641,644 A | 6/1997 | Klebe |
| 5,658,797 A | 8/1997 | Bader |
| 5,686,301 A | 11/1997 | Falkenberg et al. |
| 5,686,304 A | 11/1997 | Codner |
| 5,693,537 A | 12/1997 | Wilson et al. |
| 5,702,941 A | 12/1997 | Schwarz |
| 5,714,384 A | 2/1998 | Wilson et al. |
| 5,763,261 A | 6/1998 | Gruenberg |
| 5,763,275 A | 6/1998 | Nagels et al. |
| 5,763,279 A | 6/1998 | Schwarz et al. |
| 5,786,215 A | 7/1998 | Brown et al. |
| 5,793,440 A | 8/1998 | Nakasaka et al. |
| 5,801,054 A | 9/1998 | Kiel et al. |
| 5,866,345 A | 2/1999 | Wilding et al. |
| 5,882,918 A | 3/1999 | Goffe |
| 5,900,361 A | 5/1999 | Klebe |
| 5,912,177 A | 6/1999 | Turner et al. |
| 5,924,583 A | 7/1999 | Stevens et al. |
| 5,932,315 A | 8/1999 | Lum et al. |
| 5,942,443 A | 8/1999 | Parce et al. |
| 6,039,897 A | 3/2000 | Lochhead et al. |
| 6,048,498 A | 4/2000 | Kennedy |
| 6,096,532 A | 8/2000 | Armstrong et al. |
| 6,107,085 A | 8/2000 | Coughlin et al. |
| 6,153,073 A | 11/2000 | Dubrow et al. |
| 6,190,913 B1 | 2/2001 | Singh |
| 6,197,575 B1 | 3/2001 | Griffith et al. |
| 6,228,635 B1 | 5/2001 | Armstrong et al. |
| 6,238,908 B1 | 5/2001 | Armstrong et al. |
| 6,251,343 B1 | 6/2001 | Dubrow et al. |
| 6,274,337 B1 | 8/2001 | Parce et al. |
| 6,277,642 B1 | 8/2001 | Mentzen et al. |
| 6,297,046 B1 | 10/2001 | Smith et al. |
| 6,323,022 B1 | 11/2001 | Chang et al. |
| 6,326,211 B1 | 12/2001 | Anderson et al. |
| 6,403,369 B1 | 6/2002 | Wood |
| 6,410,309 B1 | 6/2002 | Barbera-Guillem et al. |
| 6,455,310 B1 | 9/2002 | Barbera-Guillem |
| 6,465,243 B2 | 10/2002 | Okada et al. |
| 6,468,792 B1 | 10/2002 | Bader |
| 6,481,648 B1 | 11/2002 | Zimmermann |
| 6,495,104 B1 | 12/2002 | Unno et al. |
| 6,518,035 B1 | 2/2003 | Ashby et al. |
| 6,534,013 B1 | 3/2003 | Kennedy |
| 6,548,263 B1 | 4/2003 | Kapur et al. |
| 6,551,841 B1 | 4/2003 | Wilding et al. |
| 6,555,365 B2 | 4/2003 | Barbera-Guillem et al. |
| 6,562,616 B1 | 5/2003 | Toner et al. |
| 6,569,675 B2 | 5/2003 | Wall et al. |
| 6,576,458 B1 | 6/2003 | Sarem et al. |
| 6,585,744 B1 | 7/2003 | Griffith |
| 6,585,939 B1 | 7/2003 | Dapprich |
| 6,593,136 B1 | 7/2003 | Geiss |
| 6,637,463 B1 | 10/2003 | Lei et al. |
| 6,648,015 B1 | 11/2003 | Chow |
| 6,653,124 B1 | 11/2003 | Freeman |
| 6,673,595 B2 | 1/2004 | Barbera-Guillem |
| 6,756,019 B1 | 6/2004 | Dubrow et al. |
| 6,759,245 B1 | 7/2004 | Toner et al. |
| 6,794,184 B1 | 9/2004 | Mohr et al. |
| 6,811,752 B2 | 11/2004 | Barbera-Guillem |
| 6,821,772 B2 | 11/2004 | Barbera-Guillem et al. |
| 6,846,668 B1 | 1/2005 | Garman et al. |
| 6,857,449 B1 | 2/2005 | Chow |
| 6,908,767 B2 | 6/2005 | Bader |
| 6,915,679 B2 | 7/2005 | Chien et al. |
| 6,969,166 B2 | 11/2005 | Clark et al. |
| 7,005,292 B2 | 2/2006 | Wilding et al. |
| 7,018,830 B2 | 3/2006 | Wilding et al. |
| 7,022,518 B1 | 4/2006 | Feye |
| 7,067,263 B2 | 6/2006 | Parce et al. |
| 7,141,386 B2 | 11/2006 | Dunfield et al. |
| 7,155,344 B1 | 12/2006 | Parce et al. |
| 7,160,687 B1 | 1/2007 | Kapur et al. |
| 7,171,983 B2 | 2/2007 | Chien et al. |
| 7,192,769 B2 | 3/2007 | Pykett et al. |
| 7,223,371 B2 | 5/2007 | Hayenga et al. |
| 7,343,248 B2 | 3/2008 | Parce et al. |
| 7,745,209 B2 | 6/2010 | Martin et al. |
| 7,919,319 B2 | 4/2011 | Jervis et al. |
| 8,257,964 B2 | 9/2012 | Hung et al. |
| 8,673,625 B2 | 3/2014 | Hung et al. |
| 8,709,790 B2 | 4/2014 | Hung et al. |
| 9,206,384 B2 | 12/2015 | Lee et al. |
| 9,260,688 B2 | 2/2016 | Hung et al. |
| 9,353,342 B2 | 5/2016 | Hung et al. |
| 9,353,343 B2 | 5/2016 | Hung et al. |
| 9,354,156 B2 | 5/2016 | Lee et al. |
| 9,371,929 B2 | 6/2016 | Hung et al. |
| 9,376,658 B2 | 6/2016 | Hung et al. |
| 9,388,374 B2 | 7/2016 | Hung et al. |
| 9,428,723 B2 | 8/2016 | Lee et al. |
| 9,637,715 B2 | 5/2017 | Hung et al. |
| 10,054,536 B2 | 8/2018 | Lee et al. |
| 10,138,453 B2 | 11/2018 | Hung et al. |
| 10,174,278 B2 | 1/2019 | Hung et al. |
| 10,179,897 B2 | 1/2019 | Hung et al. |
| 10,190,085 B2 | 1/2019 | Lee et al. |
| 10,526,572 B2 | 1/2020 | Hung et al. |
| 2002/0039785 A1 | 4/2002 | Schroeder et al. |
| 2002/0108860 A1 | 8/2002 | Staats |
| 2002/0110905 A1 | 8/2002 | Barbera-Guillem et al. |
| 2002/0177221 A1 | 11/2002 | Nishiguchi et al. |
| 2003/0003571 A1 | 1/2003 | Kanegasaki et al. |
| 2003/0008388 A1 | 1/2003 | Barbera-Guillem et al. |
| 2003/0008389 A1 | 1/2003 | Carll |
| 2003/0030184 A1 | 2/2003 | Kim et al. |
| 2003/0040104 A1 | 2/2003 | Barbera-Guillem |
| 2003/0124623 A1 | 7/2003 | Yager et al. |
| 2003/0143727 A1 | 7/2003 | Chang |
| 2003/0156992 A1 | 8/2003 | Anderson et al. |
| 2003/0211012 A1 | 11/2003 | Bergstrom et al. |
| 2003/0215941 A1 | 11/2003 | Campbell et al. |
| 2004/0029266 A1 | 2/2004 | Barbera-Guillem |
| 2004/0043481 A1 | 3/2004 | Wilson |
| 2004/0072278 A1 | 4/2004 | Chou et al. |
| 2004/0096960 A1 | 5/2004 | Mehta et al. |
| 2004/0132175 A1 | 7/2004 | Vetillard et al. |
| 2004/0202579 A1 | 10/2004 | Larsson et al. |
| 2004/0229349 A1 | 11/2004 | Daridon |
| 2004/0238484 A1 | 12/2004 | Le Pioufle et al. |
| 2005/0009179 A1 | 1/2005 | Gemmiti |
| 2005/0019213 A1 | 1/2005 | Kechagia et al. |
| 2005/0032208 A1 | 2/2005 | Oh et al. |
| 2005/0072946 A1 | 4/2005 | Studer et al. |
| 2005/0101009 A1 | 5/2005 | Wilson et al. |
| 2005/0106717 A1 | 5/2005 | Wilson et al. |
| 2005/0169962 A1 | 8/2005 | Bhatia et al. |
| 2005/0214173 A1 | 9/2005 | Facer et al. |
| 2005/0221373 A1 | 10/2005 | Enzelberger et al. |
| 2005/0260745 A1 | 11/2005 | Domansky et al. |
| 2005/0266582 A1 | 12/2005 | Modlin et al. |
| 2006/0003436 A1 | 1/2006 | DiMilla et al. |
| 2006/0031955 A1 | 2/2006 | West et al. |
| 2006/0112438 A1 | 5/2006 | West et al. |
| 2006/0121606 A1 | 6/2006 | Ito et al. |
| 2006/0136182 A1 | 6/2006 | Vacanti et al. |
| 2006/0141617 A1 | 6/2006 | Desai et al. |
| 2006/0154361 A1 | 7/2006 | Wikswo et al. |
| 2006/0166354 A1 | 7/2006 | Wikswo et al. |
| 2006/0199260 A1 | 9/2006 | Zhang et al. |
| 2007/0026516 A1 | 2/2007 | Martin et al. |
| 2007/0084706 A1 | 4/2007 | Takayama et al. |

(56) References Cited

U.S. PATENT DOCUMENTS

| | | |
|---|---|---|
| 2007/0090166 A1 | 4/2007 | Takayama et al. |
| 2007/0122314 A1 | 5/2007 | Strand et al. |
| 2007/0128715 A1 | 6/2007 | Vukasinovic et al. |
| 2007/0243523 A1 | 10/2007 | Ionescu-Zanetti et al. |
| 2007/0264705 A1 | 11/2007 | Dodgson |
| 2007/0275455 A1 | 11/2007 | Hung et al. |
| 2008/0032380 A1 | 2/2008 | Kleis et al. |
| 2008/0038713 A1 | 2/2008 | Gao et al. |
| 2008/0085556 A1 | 4/2008 | Graefing et al. |
| 2008/0176318 A1 | 7/2008 | Wilson et al. |
| 2008/0194012 A1 | 8/2008 | Lee et al. |
| 2008/0227176 A1 | 9/2008 | Wilson |
| 2008/0233607 A1 | 9/2008 | Yu et al. |
| 2008/0261295 A1 | 10/2008 | Butler et al. |
| 2009/0023608 A1 | 1/2009 | Hung et al. |
| 2009/0123961 A1 | 5/2009 | Meyvantsson et al. |
| 2009/0148933 A1 | 6/2009 | Battrell et al. |
| 2009/0203126 A1 | 8/2009 | Hung et al. |
| 2009/0221073 A1 | 9/2009 | Toner et al. |
| 2010/0151571 A1 | 6/2010 | Vukasinovic et al. |
| 2010/0196908 A1 | 8/2010 | Opalsky et al. |
| 2010/0234674 A1 | 9/2010 | Wheeler et al. |
| 2012/0003732 A1 | 1/2012 | Hung et al. |
| 2012/0164036 A1 | 6/2012 | Stern et al. |
| 2013/0059322 A1 | 3/2013 | Hung et al. |
| 2013/0081757 A1 | 4/2013 | Hung et al. |
| 2013/0090268 A1 | 4/2013 | Hung et al. |
| 2013/0171679 A1 | 7/2013 | Lee et al. |
| 2013/0171682 A1 | 7/2013 | Hung et al. |
| 2014/0057311 A1 | 2/2014 | Kamm et al. |
| 2014/0090735 A1 | 4/2014 | Hung et al. |
| 2014/0099705 A1 | 4/2014 | Hung et al. |
| 2014/0287489 A1 | 9/2014 | Lee et al. |
| 2016/0075984 A1 | 3/2016 | Hung et al. |
| 2016/0289623 A1 | 10/2016 | Hung et al. |
| 2016/0312166 A1 | 10/2016 | Lee et al. |
| 2016/0327470 A1 | 11/2016 | Lee et al. |
| 2016/0333297 A1 | 11/2016 | Hung et al. |
| 2016/0333298 A1 | 11/2016 | Hung et al. |
| 2016/0340630 A1 | 11/2016 | Hung et al. |
| 2017/0267961 A1 | 9/2017 | Hung et al. |

FOREIGN PATENT DOCUMENTS

| | | |
|---|---|---|
| EP | 0155237 A2 | 9/1985 |
| EP | 0725134 A2 | 8/1996 |
| EP | 0890636 A1 | 1/1999 |
| GB | 1539263 A | 1/1979 |
| WO | 91/15570 A1 | 10/1991 |
| WO | 00/56870 A1 | 9/2000 |
| WO | 00/60352 A2 | 10/2000 |
| WO | 00/78932 A1 | 12/2000 |
| WO | 01/92462 A1 | 12/2001 |
| WO | 03/085080 A1 | 10/2003 |
| WO | 03/098218 A1 | 11/2003 |
| WO | 2004/059299 A1 | 7/2004 |
| WO | 2004/106484 A2 | 12/2004 |
| WO | 2005/035728 A2 | 4/2005 |
| WO | 2007/008606 A1 | 1/2007 |
| WO | 2007/008609 A2 | 1/2007 |
| WO | 2009/089189 A2 | 7/2009 |
| WO | 2009/102453 A2 | 8/2009 |
| WO | 2012/024646 A2 | 2/2012 |

OTHER PUBLICATIONS

Final rejection dated Jul. 15, 2020 in co-pending U.S. Appl. No. 15/958,480.
Notice of allowance dated Oct. 23, 2020 in co-pending U.S. Appl. No. 15/958,480.
European communication dated Apr. 3, 2012 in co-pending European patent application No. 06786499.1
International Search Report and Written Opinion dated Apr. 9, 2009 in PCT application No. PCT/US06/26364 (corresponding to U.S. Appl. No. 11/994,997).
International Search Report and Written Opinion dated Jul. 30, 2009 in co-pending PCT application No. PCT/US2009/030168.
European communication dated Oct. 21, 2013 in co-pending European patent application No. 09701350.2.
International Search Report dated May 14, 2013 in co-pending PCT application No. PCT/US2013/024999.
International Search Report dated Mar. 19, 2013 in co-pending PCT application No. PCT/US2012/067632.
International Preliminary Report on Patentability dated Jun. 12, 2014 in co-pending PCT application No. PCT/US2012/067632.
European communication dated Jul. 28, 2015 in co-pending European patent application No. 12852539.1.
Japanese communication, with English translation, dated Nov. 17, 2015 in co-pending Japanese patent application No. 2015-503203.
Chinese communication, with English translation, dated Jun. 20, 2016 in co-pending Chinese patent application No. 201380018324.1.
Engineering Aspects of Food Biotechnology, Chapter 5, CRC Press: Boca Raton, FL, 2004, copyright 2014, p. 127, "Meet the Stem Cells; Production of Cultured Meat from a Stem Cell Biology Perspective", Brinkhof, et al., 3 pages.
Cellasic Corporation, ONIX Application Note, "Microincubator for long term live cell microscopy", Feb. 3, 2012, pp. 1-4.
Optics Express, vol. 14, No. 13, Jun. 2006, pp. 6253-6256, "Fabrication of polymer microlens arrays using capillary forming with a soft mold of micro-holes array and UV-curable polymer", Chang, et al.
Lab Chip, 2007, vol. 7, pp. 641-643, published by the Royal Society of Chemistry, "Rapid fabrication of microchannels using microscale plasma activated templating (uPLAT) generated water molds", Chao, et al.
Lab on a Chip, 2007, vol. 7, pp. 763-769, "A hydrogel-based microfluidic device for the studies of directed cell migration", Cheng, et al.
Lab Chip, 2005, vol. 5, No. 4, pp. 401-406, published by the Royal Society of Chemistry, "Human neural stem growth and differentiation in a gradient-generating microfluidic device", Chung, et al.
Lab on a Chip, 2008, vol. 9, Iss.2 pp. 269-275, "Cell Migration into Scaffolds Under Co-culture Conditions in a Microfluidic Platform," Chung et al.
J. Biochem., vol. 130, pp. 367-376, (2001), "A Method for Micrometer Resolution Patterning of Primary Culture Neurons for SPM Analysis", Degenaar, et al.
Biotechnology and Bioengineering, vol. 89, No. 1, Jan. 5, 2005, pp. 1-8, "Continuous Perfusion Microfluidic Cell Culture Array for High-Throughput Cell-Based Assays", Hung, et al.
Lab Chip, 2005, vol. 5, pp. 44-48, "A novel high aspect ratio microfluidic design to provide a stable and uniform microenvironment for cell growth in a high throughput mammalian cell culture array", Hung, et al.
Lab Chip, 2008, vol. 8, No. 1, pp. 34-57, published by the Royal Society of Chemistry, "Biomolecular gradients in cell culture systems", Keenan, et al.
Keenan et al., "A new method for studying gradient-induced neutrophil desensitization based on an open microfluidic chamber", Lab Chip, 2010, vol. 10, pp. 116-122.
Lab on a Chip, 2009, vol. 9, p. 1797-1800, "Selective and tunable gradient device for cell culture and chemotaxis study", Kim, et al.
Biotechnology and Bioengineering, vol. 97, No. 5, Aug. 1, 2007, pp. 1340-1346, "An Artificial Liver Sinusoid With a Microfluidic Endothelial-Like Barrier for Primary Hepatocyte Culture", Lee, et al.
Lab Chip, 2009, vol. 9, No. 1, pp. 164-166, published by the Royal Society of Chemistry, "Dynamic cell culture: a microfluidic function generator for live cell microscopy", Lee, et al.
Journal of the Association for Laboratory Automation (JALA), 2007, vol. 12, No. 6, pp. 363-367, "Microfluidic System for Automated Cell-Based Assays", Lee, et al.
Lee et al., "Microfluidic Systems for Live Cell Imaging", Methods in Cell Biology, 2011, vol. 102, pp. 77-103.

(56) References Cited

OTHER PUBLICATIONS

Lab Chip, 2003, vol. 3, pp. 318-323, published by the the Royal Society of Chemistry, "Fabrication of microfluidic mixers and artificial vasculatures using a high-brightness diode-pumped Nd: YAG laser direct write method", Lim, et al.

Biomed Microdevices (2008), vol. 10, pp. 499-507, "Microfluidic switching system for analyzing chemotaxis responses of wortmannin-inhibited HL-60 cells", Liu, et al.

Biomaterials, 2008, vol. 29, No. 22, pp. 3237-3244, "A gel-free 3D microfluidic cell culture system", Ong, et al.

Lab on a Chip, 2007, vol. 7, pp. 1673-1680, "Gradient generation by an osmotic pump and the behavior of human mesenchymal stem cells under the fetal bovine serum concentration gradient", Park, et al.

Angew. Chem. Int. Ed., 2004, vol. 43, pp. 1531-1536, "Minimal Functional Model of Hemostasis in a Biomimetic Microfluidic System", Runyon, et al.

Biomedical Microdevices, 2003, vol. 5, No. 3, pp. 235-244, "Microfluidic Patterning of Cellular Biopolymer Matrices for Biomimetic 3-D Structures", Tan, et al.

Office action dated Feb. 23, 2017 in co-pending U.S. Appl. No. 15/175,749.

Office action dated Nov. 1, 2017 in co-pending U.S. Appl. No. 15/175,749.

Final rejection dated Mar. 27, 2018 in co-pending U.S. Appl. No. 15/175,749.

Office action dated Jul. 10, 2018 in co-pending U.S. Appl. No. 15/175,749.

Final rejection dated Jan. 23, 2019 in co-pending U.S. Appl. No. 15/175,749.

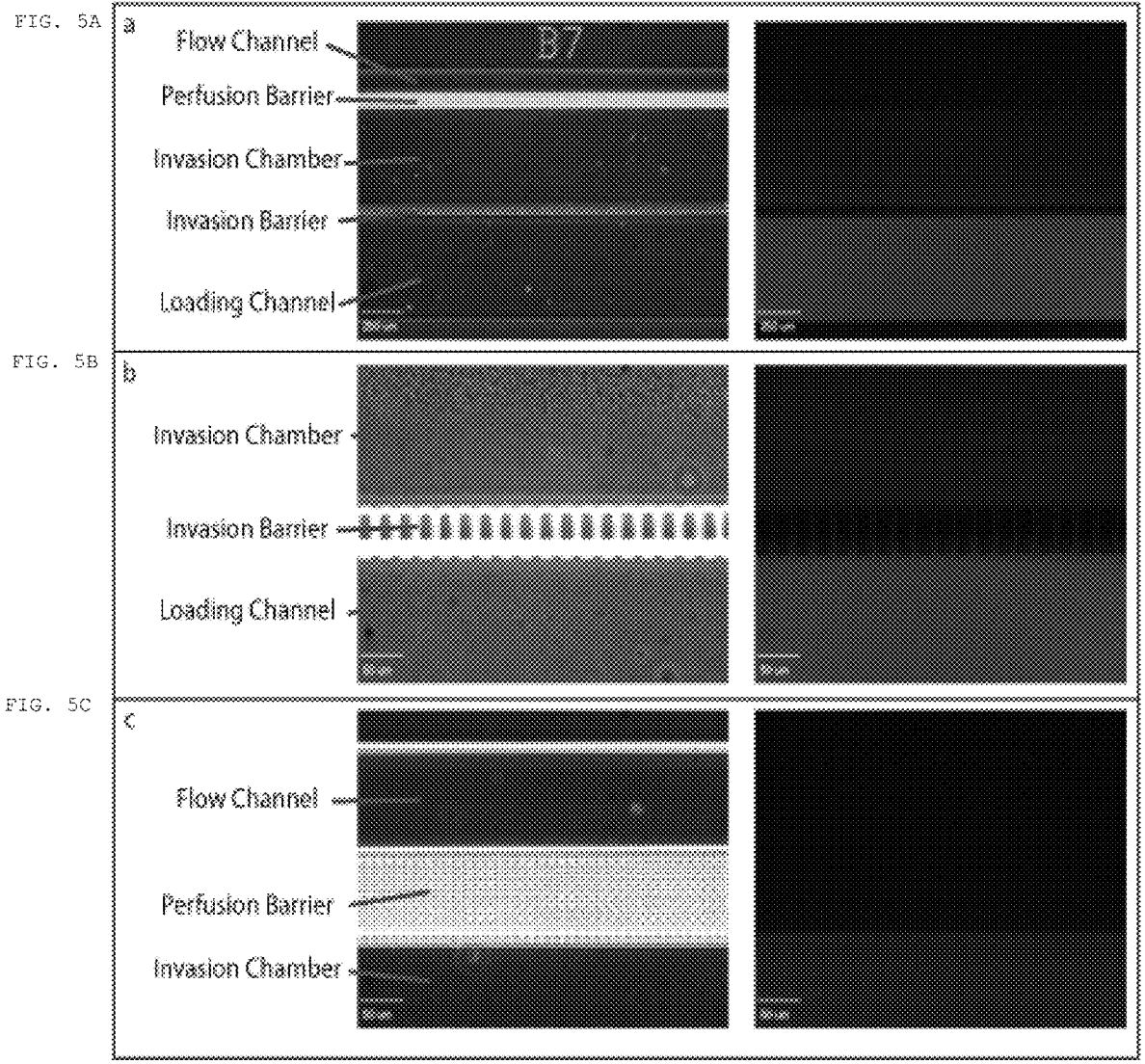

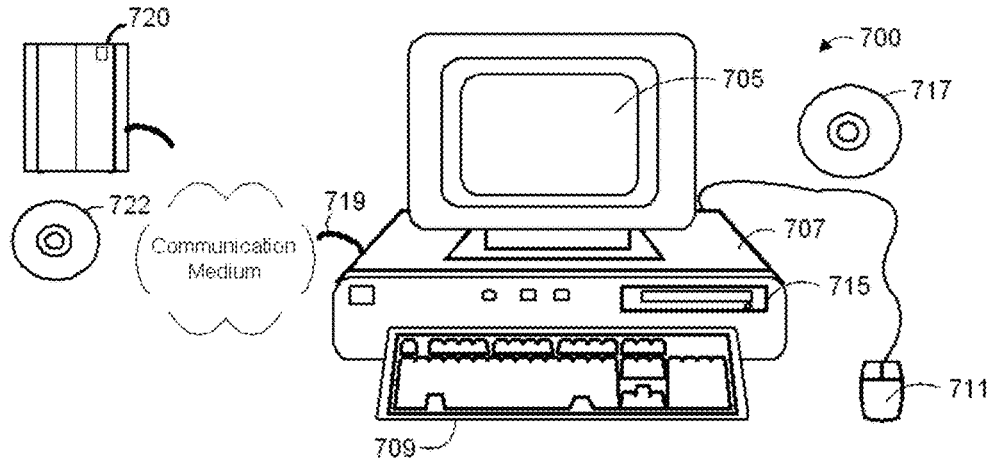

*FIG. 17*

| Disease Classification | Disease |
|---|---|
| Cardiovascular Disease | Atherosclerosis; Unstable angina; Myocardial Infarction; Restenosis after angioplasty or other percutaneous intervention; Congestive Heart Failure; Myocarditis; Endocarditis; Endothelial Dysfunction; Cardiomyopathy |
| Endocrine Disease | Diabetes Mellitus I and II; Thyroiditis; Addisson's Disease |
| Infectious Disease | Hepatitis A, B, C, D, E; Malaria; Tuberculosis; HIV; Pneumocystis Carinii; Giardia; Toxoplasmosis; Lyme Disease; Rocky Mountain Spotted Fever; Cytomegalovirus; Epstein Barr Virus; Herpes Simplex Virus; Clostridium Dificile Colitis; Meningitis (all organisms); Pneumonia (all organisms); Urinary Tract Infection (all organisms); Infectious Diarrhea (all organisms) |
| Angiogenesis | Pathologic angiogenesis; Physiologic angiogenesis; Treatment induced angiogenesis |
| Inflammatory/Rheumatic Disease | Rheumatoid Arthritis; Systemic Lupus Erythematosis; Sjogrens Disease; CREST syndrome; Scleroderma; Ankylosing Spondylitis; Crohn's; Ulcerative Colitis; Primary Sclerosing Cholangitis; Appendicitis; Diverticulitis; Primary Biliary Sclerosis; Wegener's Granulomatosis; Polyarteritis nodosa; Whipple's Disease; Psoriasis; Microscopic Polyanngiitis; Takayasu's Disease; Kawasaki's Disease; Autoimmune hepatitis; Asthma; Churg-Strauss Disease; Beurger's Disease; Raynaud's Disease; Cholecystitis; Sarcoidosis; Asbestosis; Pneumoconioses |
| Transplant Rejection | Heart; Lung; Liver; Pancreas; Bowel; Bone Marrow; Stem Cell; Graft versus host disease; Transplant vasculopathy |
| Leukemia and Lymphoma | |

*FIG. 18 (TABLE 1)*

CELL CULTURE AND INVASION ASSAY METHOD AND SYSTEM

CROSS REFERENCE TO RELATED APPLICATIONS

This application is a continuation of U.S. patent application Ser. No. 15/459,332 filed Mar. 15, 2017, which is a divisional of U.S. patent application Ser. No. 13/436,992 filed on Apr. 1, 2012 (now U.S. Pat. No. 9,637,715 issued May 2, 2017), which claims priority from provisional patent application No. 61/471,103, Cell Culture And Invasion Assay Method And System, filed Apr. 1, 2011. The disclosures of which are incorporated herein by reference in its entireties.

This application is related to material discussed in one or more of the following applications, each of which are incorporated herein by reference for all purposes: provisional patent application 61/367,371 filed Jul. 23, 2010, provisional patent application 61/297,278 filed Jan. 21, 2010, provisional patent application 61/037,297 filed Mar. 17, 2008, provisional patent application 61/018,882 filed Jan. 3, 2008, U.S. application Ser. No. 11/994,997, filed Aug. 11, 2008, which is a National Stage Entry of PCT/US06/26364, filed Jul. 6, 2006 and which claims priority from provisional patent application 60/773,467 filed 14 Feb. 2006 and from provisional patent application 60/697,449 filed 7 Jul. 2005, U.S. application Ser. No. 12/019,857, filed Jan. 25, 2008, which claims priority to U.S. Provisional Patent Application No. 60/900,651 filed on Feb. 8, 2007, U.S. application Ser. No. 11/648,207, filed Dec. 29, 2006, which claims priority to U.S. Provisional Patent Application No. U.S. provisional patent application No. 60/756,399 filed on Jan. 4, 2006, U.S. application Ser. No. 12/348,907, filed 5 Jan. 2009.

COPYRIGHT NOTICE

Pursuant to 37 C.F.R. 1.71(e), applicants note that a portion of this disclosure contains material that is subject to copyright protection (such as, but not limited to, diagrams, device photographs, or any other aspects of this submission for which copyright protection is or may be available in any jurisdiction.). The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The invention in various embodiments relates to assays, systems, and devices for detecting invasion behavior of cells or related behaviors of other micro-objects using microfluidic systems. Particular embodiments involve configurations that can be used with various standard automated handling systems, with active or passive loading and perfusion of medium and to provide high-throughput multi-assay automated systems for analyzing cell invasion, movement, chemotaxis or other properties.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

Microfluidic cell culture is an important technology for applications in drug screening, tissue culturing, toxicity screening, and biologic research and can provide improved biological function, higher-quality cell-based data, reduced reagent consumption, and lower cost. High quality molecular and cellular sample preparations are important for various clinical, research, and other applications. In vitro samples that closely represent their in vivo characteristics can potentially benefit a wide range of molecular and cellular applications. Handling, characterization, culturing, and visualization of cells or other biologically or chemically active materials (such as beads coated with various biological molecules) has become increasingly valued in the fields of drug discovery, disease diagnoses and analysis, and a variety of other therapeutic and experimental work.

Numerous aspects related to microfluidic systems, devices, methods and manufacturing are discussed in the above-referenced and related patent applications. While no particular limitations should be read form those applications into any claims presented herein, these incorporated documents provide useful background material related to specific embodiments.

One area of interest in cellular assay systems are assays that are able to determine characteristics of cellular migration. Such assays are important in characterization of various types of malignant cells and also in characterization of other cells under various stimulations.

Some assays using microchambers or microfluidics have been proposed. Other systems use standard culture plates with various barrier inserts to attempt to detect cellular invasion. Currently available systems, however, have failed with regard to a number of aspects necessary for ease-of-use, high-throughput, or automated applications.

Other publications and/or patent documents that discuss various strategies related to cell culture using microfluidic systems and related activities include the following U.S. patent applications and non-patent literature, which, along with all citations therein, are incorporated herein by reference for all purposes. A listing of these references here does not indicate the references constitute prior art.

Cytoplex, Inc. U.S. Pat. No. 6,653,124 "Array-based microenvironment for cell culturing, cell monitoring and drug-target validation."

Cellomics, Inc. U.S. Pat. No. 6,548,263 "Miniaturized cell array methods and apparatus for cell-based screening."

Fluidigm, Inc. Published Application 20040229349 (Nov. 18, 2004) "Microfluidic particle-analysis systems."

OTHER REFERENCES

1. T. H. Park and M. L. Shuler, Biotechnol. Prog., 2003, 19, 243.
2. G. M. Walker, H. C. Zeringue and D. J. Beebe, Lab Chip, 2004, 4, 91.
3. E. Leclerc, Y. Sakai and T. Fujii, Biotechnol. Prog., 2004, 20, 750.
4. M. J. Powers, K. Domansky, M. R. Kaazempur-Mofrad, A. Kalezi, A. Capitano, A. Upadhyaya, P. Kurzawski, K. E. Wack, D. B. Stolz, R. Kamm and L. G. Griffith, Biotechnol. Bioeng., 2002, 78, 257.
5. K. Viravaidya and M. L. Shuler, Biotechnol. Prog., 2004, 20, 590.
6. Y. Kostov, P. Harms, L. Randers-Eichhorn and G. Rao, Biotechnol. Bioeng., 2001, 72, 346.

7. N. Li Jeon, H. Baskaran, S. K. Dertinger, G. M. Whitesides, L. Van der Water and M. Toner, Nat. Biotechnol., 2002, 20, 826.
8. T. Thorsen, S. J. Maerkl and S. R. Quake, Science, 2002, 298, 580.
9. H. Andersson and A. van den Berg, Lab Chip, 2004, 4, 98.
10. Dove, A. (2003) Nature Biotechnology 21, 859-864.
11. Entzeroth, M. (2003) Current Opinion in Pharmacology 3, 522-529.
12. Boess, F.; Kamber, M.; Romer, S.; Gasser, R.; Muller, D.; Albertini, S.; Suter, L. Toxicol Sci 2003, 73, (2), 386-402.
13. Rodriguez-Antona, C.; Donato, M. T.; Boobis, A.; Edwards, R. J.; Watts, P. S.; Castell, J. V.; Gomez-Lechon, M. J. Xenobiotica 2002, 32, (6), 505-20.
14. Cukierman, E.; Pankov, R.; Stevens, D. R.; Yamada, K. M. Science 2001, 294, (5547), 1708-12.
15. Griffith, L. G.; Swartz, M. A. Nat Rev Mol Cell Biol 2006, 7, (3), 211-24.
16. Revzin, A.; Rajagopalan, P.; Tilles, A. W.; Berthiaume, F.; Yarmush, M. L.; Toner, M. Langmuir 2004, 20, (8), 2999-3005.
17. Flaim, C. J.; Chien, S.; Bhatia, S. N. Nat Methods 2005, 2, (2), 119-25.
18. Anderson, D. G.; Levenberg, S.; Langer, R. Nat Biotechnol 2004, 22, (7), 863-6.
19. Battle, T.; Stacey, G. Cell Biol Toxicol 2001, 17, (4-5), 287-99.
20. LeCluyse, E. L.; Bullock, P. L.; Parkinson, A. Advanced Drug Delivery Reviews 1996, (22), 133-186.
21. Ben-Ze'ev, A.; Robinson, G. S.; Bucher, N. L.; Farmer, S. R. Proc Natl Acad Sci USA 1988, 85, (7), 2161-5.
22. Bhatia, S. N.; Balis, U. J.; Yarmush, M. L.; Toner, M. Faseb J 1999, 13, (14), 1883-900.
23. Berthiaume, F.; Moghe, P. V.; Toner, M.; Yarmush, M. L. Faseb J 1996, 10, (13), 1471-84.
24. Stevens, M. M.; George, J. H. Science 2005, 310, (5751), 1135-8.
25. Bissell, M. J.; Rizki, A.; Mian, I. S. Curr Opin Cell Biol 2003, 15, (6), 753-62.
26. Allen, J. W.; Bhatia, S. N. Biotechnol Bioeng 2003, 82, (3), 253-62.
27. Hung, P. J.; Lee, P. J.; Sabounchi, P.; Aghdam, N.; Lin, R.; Lee, L. P. Lab Chip 2005, 5, (1), 44-8.
28. Lee, P. J.; Hung, P. J.; Rao, V. M.; Lee, L. P. Biotechnol Bioeng 2005.
29. Puhl, G.; Schaser, K. D.; Vollmar, B.; Menger, M. D.; Settmacher, U. Transplantation 2003, 75, (6), 756-61.
30. Park, J.; Berthiaume, F.; Toner, M.; Yarmush, M. L.; Tilles, A. W. Biotechnol Bioeng 2005, 90, (5), 632-44.
31. Anderson, K.; Wilkinson, R.; Grant, M. H. Int J Artif Organs 1998, 21, (6), 360-4.
32. Landry, J.; Bernier, D.; Ouellet, C.; Goyette, R.; Marceau, N. J Cell Biol 1985, 101, (3), 914-23.
33. A. Ben-Ze'ev, G. S. Robinson, N. L. Bucher, S. R. Farmer, Proc Natl Acad Sci USA 85, 2161 (April, 1988).
34. J. Landry, D. Bemier, C. Ouellet, R. Goyette, N. Marceau, J Cell Biol 101, 914 (September, 1985).
35. S. A. Stoehr, H. C. Isom, Hepatology 38, 1125 (November, 2003).
36. Zhang, X, Wang, W, Yu, W, Xie, Y, Zhang, X, Zhang, Y, Ma, X. Biotechnol Prog 2005, 21, 1289-96.
37. Kelm, J, Timmins, N, Brown, C, Fussenegger, M, Nielsen, L. Biotechnology and Bioengineering. 2003, 83(2)173-180.
38. Kuns-Schughart, L, Freyer, J, Hofstaedter, F, Ebner, R. J. Biomolecular Screening. 2004, 9(4) 273-285.

Earlier work and patent applications as cited above, involving at least one of the present inventors, discuss various configurations, methods, and systems related to microfluidic cell culture and that work and those publications are incorporated herein by reference.

SUMMARY

The present invention involves various components, systems, and methods related to improved microfluidic cell culture devices and systems, in particular systems for the culturing and analysis of invasive or otherwise metastatic or motile cells. In one aspect, the invention involves novel microfluidic cell culture devices, systems and methods that have advantages over previously proposed invasion assays using either multi-culture chamber plates or microfluidic structures. In another aspect, the invention involves novel structures and methods for integrating multiple microfluidic cell culture and/or cell invasive assay units into various multi cell culture unit systems, such as to a microtiter well plate structure including various standard well plate formats (e.g., a 96-well SBS culture plate, or other plate formats, including plates having 6, 12, 24, 96, 384 or 1536 sample wells, as well as open bottom standard well plates, allowing for attachment to microfluidic structures as described herein.).

In a further aspect, the invention involves novel fabrication methods for creating an array of microfluidic cell culture units or areas suitable for integration with a well plate wherein structures for cell culture, cell loading, medium feeding, and invasion and perfusion barriers are all fabricated using one set of process steps. In another aspect, the invention involves novel systems, methods, and components for an improved automated high-throughput cell culture and/or screening and/or assay system using microfluidic cell culture devices and systems. In other aspects, the invention involves novel culture chamber designs and systems for providing effective culture of cells in various situations, including cells cultured in a gel 3D matrix.

In particular embodiments and examples, design features include providing an invasion assay device in a convenient format that allows for the elimination of tubing and connectors to the plates themselves, the ability to maintain long-term continuous perfusion cell culture using a passive grvity-driven flow, the ability to perform direct analysis on the outlet wells and/or cellular invasion observation wells or culture wells of the microfluidic plate, the ability to effectively handle gel culture media.

While many of the examples discussed in detail herein are designed to be used in conjunction with a standard or custom well plate, the microfluidic structures and culture units and systems and methods of various configurations as described herein can also be deployed independently of any well-plate, such as in various integrated lab-on-a-chip systems that are not configured to be used in conjunction with well plates or various other microfluidic devices or systems.

For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents.

Furthermore, it is well known in the art that systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification. Unless specifically stated otherwise herein, any combination of elements described herein should be understood to include every sub-combination of any subset of those elements and also any sub-combination of any subset of those elements combined with any other element described herein as would be understood to a practitioner of skill in the art.

In some of the drawings and detailed descriptions below, the present invention is described in terms of the important independent embodiments of multi-component devices or systems. This should not be taken to limit various novel aspects of the invention, which, using the teachings provided herein, can be applied to a number of other situations. In some of the drawings and descriptions below, the present invention is described in terms of a number of specific example embodiments including specific parameters related to dimensions of structures, pressures or volumes of liquids, temperatures, electrical values, durations of time, and the like. Except where so provided in the attached claims, these parameters are provided as examples and do not limit the invention, which encompasses other devices or systems with different dimensions. For purposes of providing a more illuminating description, particular known fabrication steps, cell handling steps, reagents, chemical or mechanical process, and other known components that may be included to make a system or manufacture a device according to specific embodiments of the invention are given as examples. It will be understood to those of skill in the art that except were specifically noted herein otherwise, various known substitutions can be made in the processes described herein.

All references, publications, patents, and patent applications cited in this submission are hereby incorporated by reference in their entirety for all purposes.

BRIEF DESCRIPTION OF THE DRAWINGS

FIGS. 5A-5C are a series of micrographs of regions of the invasion chamber after loading with gel to show invasion assay operation according to specific embodiments of the invention.

FIG. 17 is a block diagram showing a representative example logic device in which various aspects of the present invention may be embodied.

FIG. 18 (Table 1) illustrates an example of diseases, conditions, or states that can evaluated or for which drugs or other therapies can be tested according to specific embodiments of the present invention.

DETAILED DESCRIPTION OF SPECIFIC EMBODIMENTS

1. Overview

Definitions

Figure 1A:
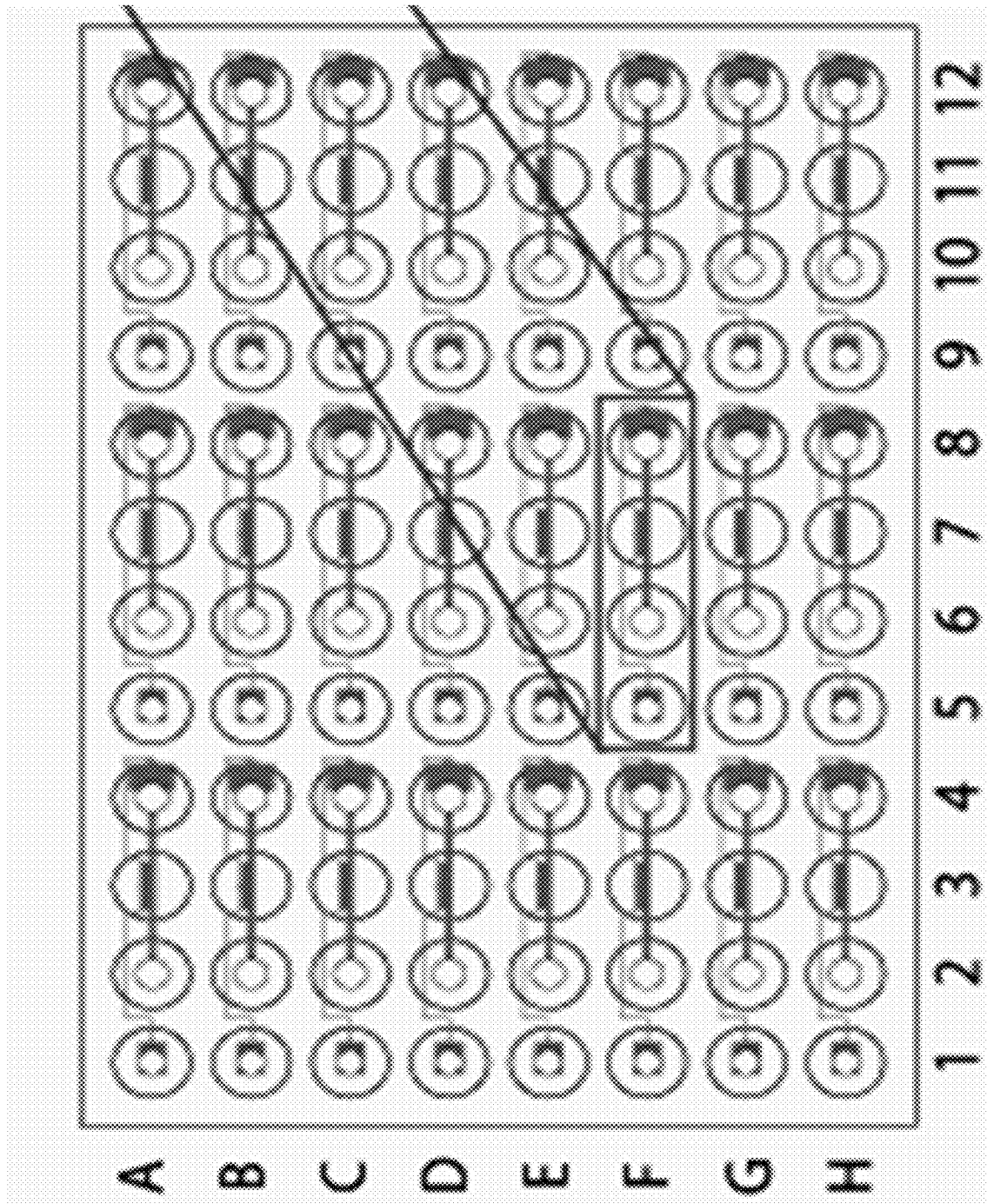
FIG. 1A is a schematic diagram of an example microfluidic plate design according to specific embodiments of the invention, in this example having 24 invasion assay units on a 96 well plate, each unit in this example containing 4 wells: a flow inlet, a cell/gel inlet, an invasion chamber, and a flow outlet.

A "particle" refers to biological cells, such as mammalian or bacterial cells, viral particles, or liposomal or other particles that may be subject to assay in accordance with the invention. Such particles have minimum dimensions between about 50-100 nm, and may be as large as 20 microns or more. When used to describe a cell assay in accordance with the invention, the terms "particles" and "cells" may be used interchangeably.

A "microchannel" or "channel" or "flow channel" generally refers to a micron-scale channel used for fluidically connecting various components of systems and devices according to specific embodiments of the invention. A microchannel typically has a rectangular, e.g., square, or rounded cross-section, with side and depth dimensions in a preferred embodiment of between 10 and 500 microns, and 10 and 500 microns, respectively. Fluids flowing in the microchannels may exhibit microfluidic behavior. When used to refer to a microchannel within the microwell array device of the invention, the term "microchannel" and "channel" are used interchangeably. "Flow channel" generally denotes channels designed for passage of media, reagents, or other fluids or gels and in some embodiments cells. "Culture channel" or "cell culture channel" generally denotes a portion of a cell culture structure that cells are designed to flow through and also remain during cell culture (though the cells may be localized into a particular culture area of the culture channel in some embodiments). "Air channel" generally denotes a roughly micron-scale channel used for allowing gases, such as air, oxygen enriched mixtures, etc., to pass in proximity to flow channels or culture areas. "Perfusion channel" is sometimes used to indicate a flow channel and any perfusion passages or structures that allow media to perfuse to the culture area.

A "perfusion barrier" refers to a combination of solid structures and perfusion passages that generally separate a flow channel from a cell culture area or chamber. The perfusion passages are generally smaller than the microchannel height and/or width (for example, on the order of 5-50% or on the order of about 10%) and are designed to keep cells, other culture items, and in some embodiments gels, from migrating into the flow channels, while allowing some fluidic flow that is generally of a much higher fluidic resistance than the fluid flow in the flow channels. In one example embodiment, the perfusion barrier has a perfusion passage that is 4 microns high and that otherwise runs most of the length of the microchannel. In other embodiments, a perfusion barrier has many perfusion passages that are about as high as the microfluidic channel, but about 4 microns wide.

A "microfluidics device" refers to a device having various station or wells connected by micron-scale microchannels in which fluids will exhibit microfluidic behavior in their flow through the channels.

A "microwell array" refers to an array of two or more microwells formed on a substrate.

A "device" is a term widely used in the art and encompasses a broad range of meaning. For example, at its most basic and least elaborated level, "device" may signify simply a substrate with features such as channels, chambers and ports. At increasing levels of elaboration, the "device" may further comprise a substrate enclosing said features, or other layers having microfluidic features that operate in concert or independently. At its most elaborated level, the "device" may comprise a fully functional substrate mated with an object that facilitates interaction between the external world and the microfluidic features of the substrate. Such an object may variously be termed a holder, enclosure, housing, or similar term, as discussed below. As used herein, the term "device" refers to any of these embodiments or levels of elaboration that the context may indicate.

Microfluidic systems provide a powerful tool to conduct biological experiments. Recently, elastomer-based microfluidics has especially gained popularity because of its optical transparency, gas permeability and simple fabrication methods. However, the interface with the end-users requires labor-intensive hole punching through the elastomer, and additional steps of tubing and syringe pump connection.

The present invention involves integrated microfluidics used for various culture and assay applications. The invention further involves methods of manufacture of microfluidics and components and a system for automating cell culture using such plates. Advantages of specific embodiments include use of a standard microtiter plate format, tubing free cell culture, and a biomimetic microenvironment for assaying invasion, migration, or chemotaxic cellular behavior.

A system according to specific embodiments of the invention (for example, using 96-well standard plates) can be operated using standard techniques and equipment for handling standard microtiter plates, as are well known in the art. For example, liquid and/or gel or cell dispensing is achieved with standard pipette mechanics, and cell culture and analysis can be made compatible with existing incubators and plate readers.

According to further embodiments of the invention, a novel cell loading system uses a pneumatic manifold and pneumatic pressure to place cells in the micro culture area. With the addition of this cell loading system, microfluidic cell culture and analysis can be fully automated using other automated equipment that exists for handling standard titer plates.

In further embodiments, the gravity driven flow culture configuration utilizes the medium level difference between the inlet and outlet well as well as engineering the fluidic resistances to achieve the desirable flow rate in nL/min regime. This provides the significant advantage of being able to "passively" flow culture medium for long periods of time (e.g., up to 4 days) without the use of bulky external pumps or tubes, which in the case of invasive assays allows for easy set up of the assay and easy reading of invasive assay results at one or more time periods after culture initiation.

In further embodiments, the invention involves a microfluidic system to allow control of the cell culture environment for long-term time-lapse microscopy of adherent and/or invasive or migrating cells. According to specific embodiments of the invention, the invention provides a multiplexed microfluidic flow chamber allowing for time-lapse microscopy experimentation and examination of cell invasion among other assays. The microfluidic chamber uses a perfusion barrier to separate cells from flow channels and an invasion barrier to study the invasive properties of cells between an culture chamber and an invasion chamber. Example embodiments are formatted to a standard well plate, allowing liquid and cell/gel samples to be directly pipetted into the appropriate inlet reservoirs using standard equipment.

In some embodiments, a custom pneumatic flow controller can be used to load the cells into the culture regions as well as to switch between different exposure solutions. A digital software interface can be used to allow a user to program specific inputs (pulses, ramps, etc.) over time to expose the cells to complex functions during time-lapse imaging.

Dynamic responses in living cells are the foundation for phenomena such as biological signal processing, gene expression regulation, differentiation, and cell division. In specific embodiments, the invention involves a system capable of controlling the cellular micro-environment in a multiplexed format compatible with current cell culture methods. Cell response can be quantified using high magnification fluorescence microscopy to derive kinetic information with sub-cellular resolution. This capability has broad applications in cellular systems biology where dynamic single cell response experiments are not currently practical. While some invasion assay embodiments according to specific embodiments can use mostly or fully passive systems with exposure to just one medium/reagent mixture other invasion assays according to specific embodiments can be performed using complex reagent scheduling using a manifold as described herein.

2. Microfluidic Culture System and Array

The applications referenced above discussed a variety of different cell culture configurations and fabrication techniques. Portions of the operation of the cell culture areas and materials are useful as background to the present discussion. In some examples therein, one or more micro culture areas are connected to a medium or reagent channel via a grid of fluidic passages (or diffusion inlets or conduits), wherein the grid comprises a plurality of intersecting high fluidic resistance perfusion passages. In one discussed example, passages in the grid are about 1 to 4 μm in height, 25 to 50 μm in length and 5 to 10 μm in width, the grid allowing for more even diffusion between medium or reagent channels and the culture area and allowing for easier manufacturing and more even diffusion. The earlier application further discussed that the high fluidic resistance ratio between the microchamber and the perfusion/diffusion passages or grid (e.g., ratios in the range of about 10:1, 20:1 to 30:1) offers many advantages for cell culture such as: (1) size exclusion of cells; (2) localization of cells inside a microchamber; (3) promoting a uniform fluidic environment for cell growth; (4) ability to configure arrays of microchambers or culture areas; (4) ease of fabrication, and (5) manipulation of reagents without an extensive valve network. Examples were illustrated wherein a grid-like perfusion barrier can be much shorter than the culture area or can be near to or at the same height, according to specific embodiments of the invention and further wherein various configurations for culture devices were illustrated.

3. Invasion Assay Unit

In specific embodiments, the invention further comprises a microfluidic plate for 3D cancer cell invasion assays. In specific example implementations, the plate uses the standard 96 well plate format with 4 wells connected by microfluidic channels to create each individual flow and invasion assay unit (with, e.g., 24 units per plate in specific embodiments). In some embodiments, flows are driven by capillary force and gravity as discussed elsewhere herein, allowing the plates to be operated in a standard incubator with no external connections after initial introduction of cells and culture media. In specific embodiments, a device of the invention receives cells in a 3D gel into a culture chamber. The culture chamber is separated by an invasion barrier from an invasion chamber and both are separated from the flow channel by a set of, for example, 8×8 micron cross section microfluidic pores or passages (at times herein referred to as the invasion barrier) thus modeling the in vivo environment for tumor invasion.

FIG. 1A is a schematic diagram of an example microfluidic plate design according to specific embodiments of the invention, in this example having 24 invasion assay units on a 96 well plate, each unit in this example containing 4 wells: a flow inlet, a cell/gel inlet, an invasion chamber, and a flow outlet. In this embodiment, liquid in the flow inlet, cell/gel inlet, and flow outlet are in contact with the microchannels. The well above the invasion chamber is left empty for better imaging quality. The bottom surface of the plate is a glass slide. There are 24 flow units per plate (each unit is 1 well by 4 wells, forming an 8×3 array on the 8×12 well plate).

Figure 1B:
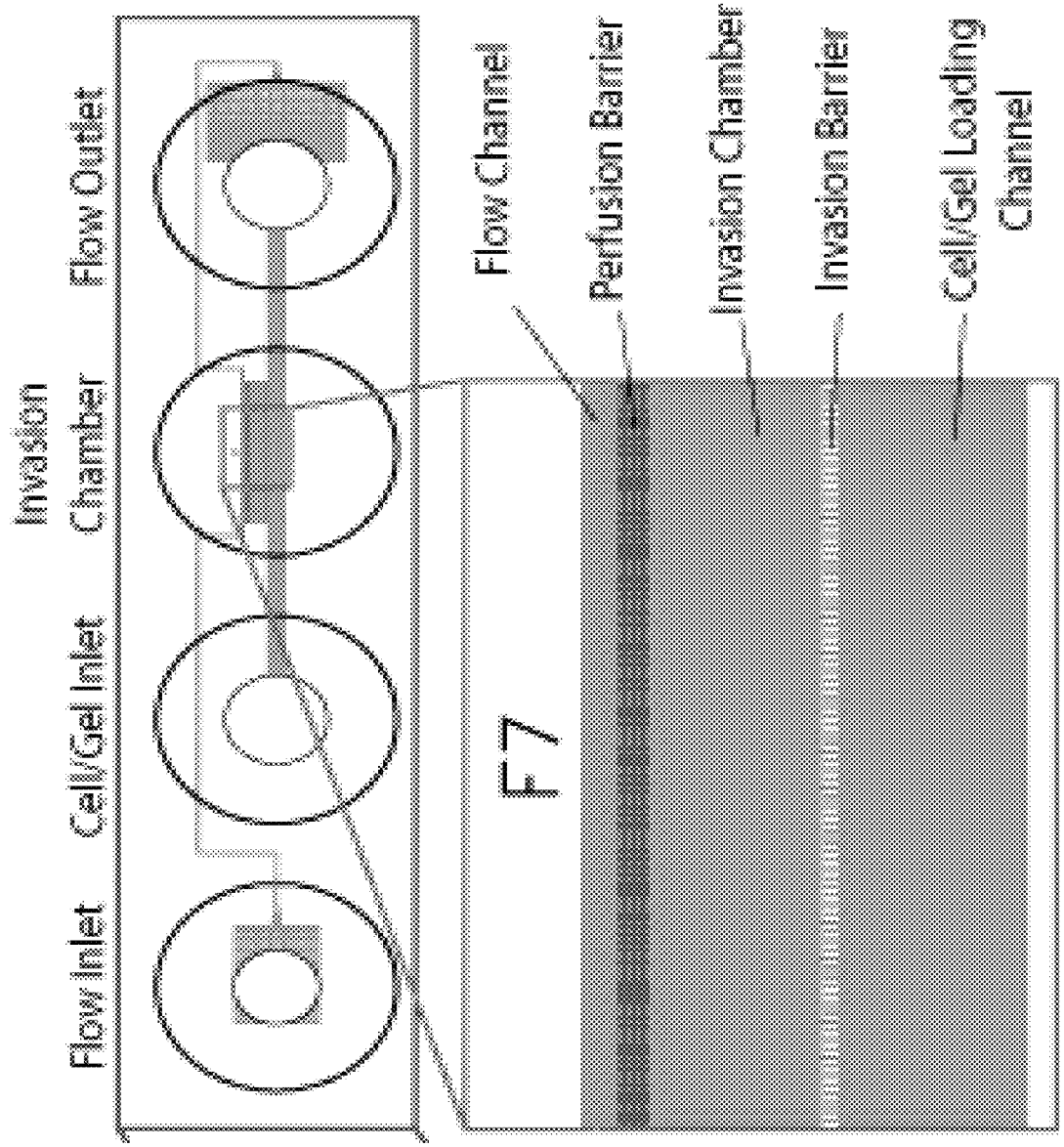
FIG. 1B is a schematic diagram showing details of one invasion culture unit according to specific embodiments of the invention.

Returning to the schematic shown in FIGS. 1A-1B, the figure provides three levels of magnification. The most magnified region, labeled F7 in FIGS. 1A-1B to indicate the particular well position in the example 96 well plate, shows details of one invasion chamber according to specific embodiments. This invasion assay/culture area can be understood as comprising 5 primary regions.

A cell/gel loading channel is shown at the bottom of the figure. According to specific embodiments, cells mixed in a gel (e.g. Matrigel, collagen, fibrin, etc.) are loaded into the bottom channel, either by capillary flow or using other active or passive loading means as described herein. In operation, the channel is designed so that the gel fills the loading channel and also fills the invasion barrier and part or all of the invasion chamber, but not past the perfusion barrier. In one example embodiment, the loading channel is 550 μm in width and 50 μm in height.

According to specific embodiments, the loading channel is separated from an invasion chamber by an invasion barrier. In a specific example, the invasion barrier consists of a network of channels of approximately 50×8×8 μm (L×W×H) dimensions. These are or become filled with gel or liquid in some embodiments and mimic the endothelial barrier in tissue. Invasive cancer cells are able to move through the narrow channels of the invasion barrier into the invasion chamber. The invasion chamber in this example about 4.8×0.5×0.05 mm in dimension (L×W×H) and is used to count the number of cells that invade or migrate from the loading channel past the invasion barrier. During assay operation, cells in this chamber can be counted by manual or automated microscope or other means and quantified to determine an invasion index for the well.

The perfusion barrier is a network of channels of, in specific embodiments, dimensions of 100×4×2 μm (L×W×H), that separates the invasion chamber from the flow channel. The narrow cross section prevents cells and gels from passing through the infusion barrier. Medium (and drugs carried in the medium, including chemoattractants, dyes, or other materials used in an invasion assay or in cell culture) diffuse across the perfusion barrier and form a gradient to the invading cells, modeling the tumor environment in the vasculature.

An 100×50 μm (W×H) flow channel carries fluid from the flow inlet well past the invasion chamber and empties to the flow outlet well. Diffusion of nutrients from the flow through the perfusion barrier feeds the cells. This channel simulates the blood flow in the body. In a particular example embodiment, the gravity driven flow rate is set to ~20 μl/day, allowing for >3 day continuous flow experiments without refilling the wells.

As stated above, dimensions provided herein are for an example culture unit. According to various specific embodiments, any dimensions suitable for a particular media or culture item can be used in accordance with other teachings provided herein.

4. Invasion Assay Plate

Figure 2A:
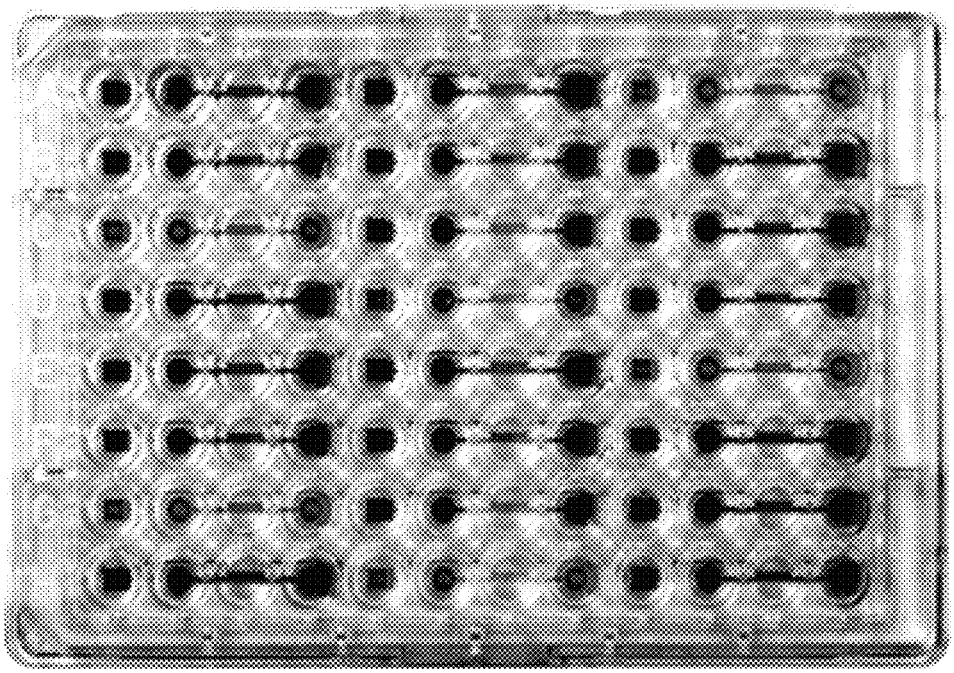
FIGS. 2A-2B are photos illustrating an example 96 well invasion plate, showing the 24 flow units filled with colored dyes, with FIG. 2A showing an image taken from the top of the plate and FIG. 2B showing an image taken from the bottom of the plate, in this example a 96-well standard SBS plate is used to illustrate specific embodiments.
Figure 2B:
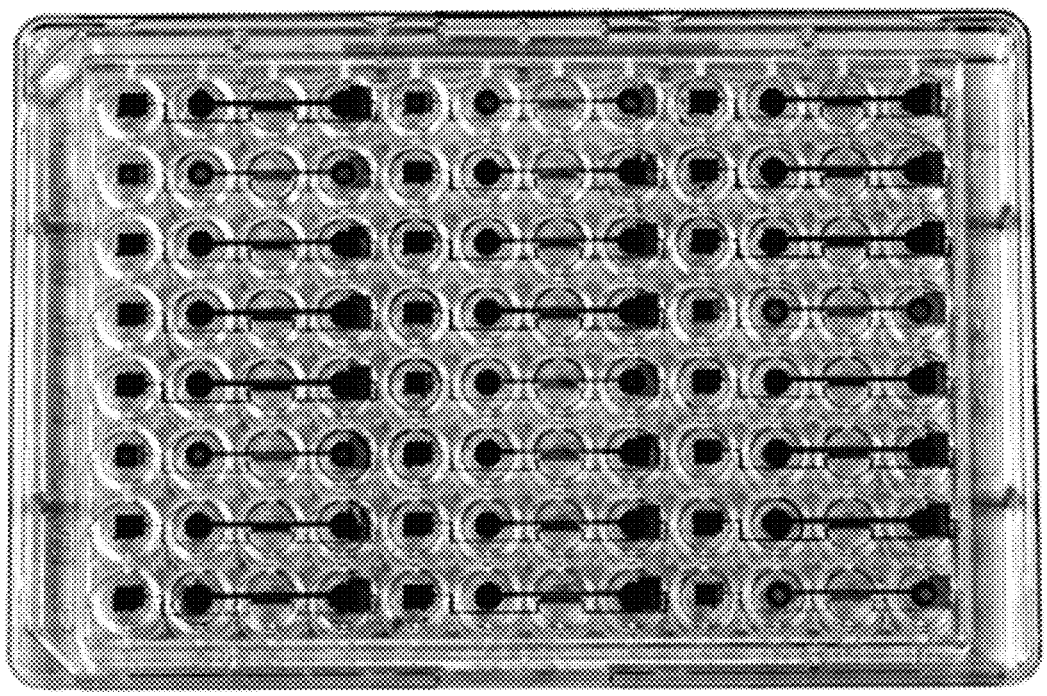

FIGS. 2A-2B are photos illustrating an example 96 well invasion plate, showing the 24 flow units filled with colored dyes, with FIG. 2A showing an image taken from the top of the plate and FIG. 2B showing an image taken from the bottom of the plate, in this example a 96-well standard SBS plate is used to illustrate specific embodiments. According to specific embodiments, the invasion assay unit as described above is configured into a standard culture well plate to allow for simultaneous running of multiple invasion assay experiments. These experiments can include multiple assays for a single subject, either of the same or different tissue samples, multiple assays from different subjects, and can include assays that expose cells to different media, hormonal or other stimuli, drugs, chemoattractants, etc.

While an example of a 4-well assay unit on a 96 well-plate is shown, different unit sizes and different culture plate sizes can also embody the invention as will be clear from the discussions provided herein and in related incorporated applications.

Figure 3A:
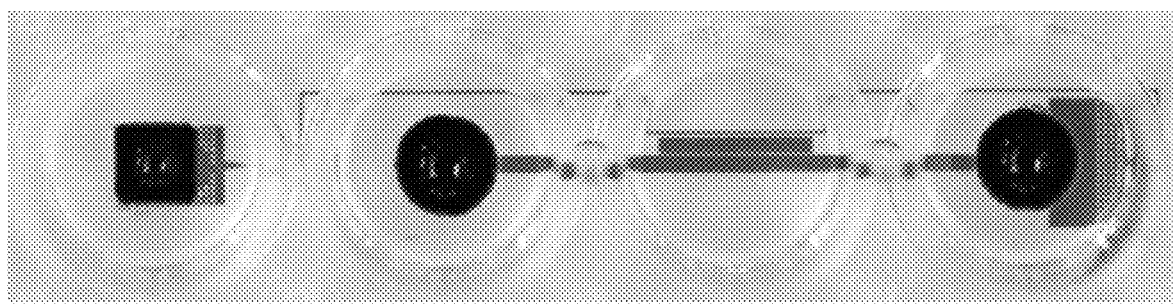
FIGS. 3A-3B are photos illustrating an example single flow unit filled with blue dye with the image taken from top (FIG. 3A) and bottom (FIG. 3B), with the bottom picture taken by flipping the plate in the up-down direction, so that the inlet well is on the left in both pictures.
Figure 3B:
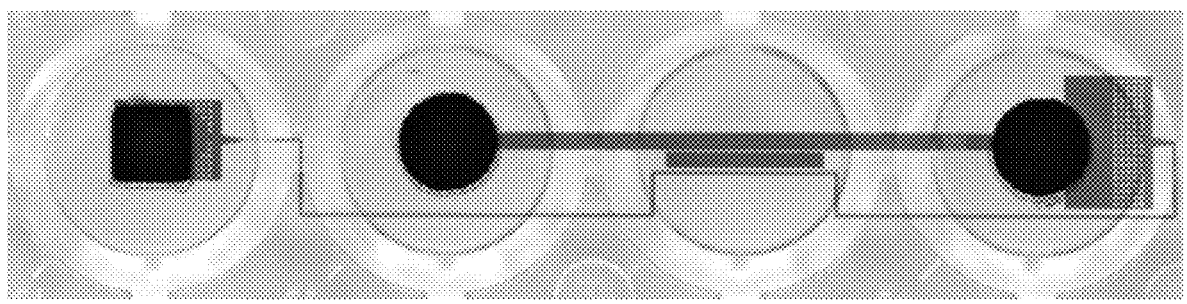

FIGS. 3A-3B are photos illustrating an example single flow unit filled with blue dye with the image taken from top (FIG. 3A) and bottom (FIG. 3B), with the bottom picture taken by flipping the plate in the up-down direction, so that the inlet well is on the left in both pictures.

5. Example Operation

Figure 4A:
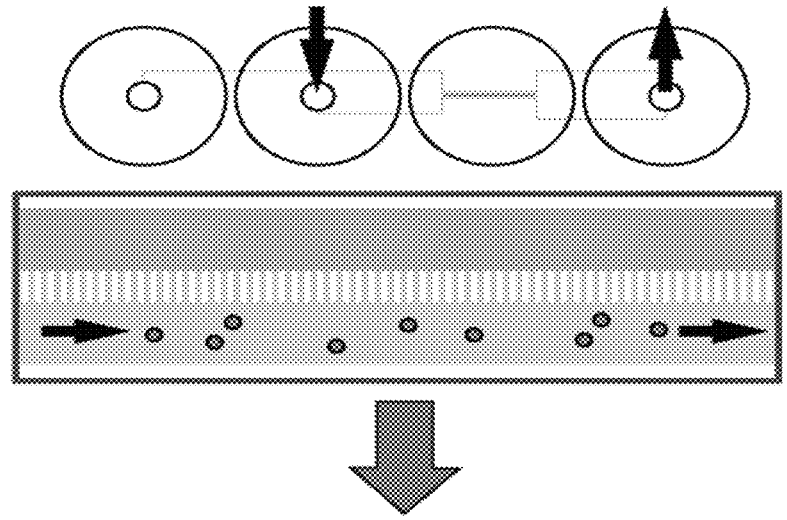
FIGS. 4A-4C are a set of schematics illustrating an example of invasion plate operation according to specific embodiments.
Figure 4B:
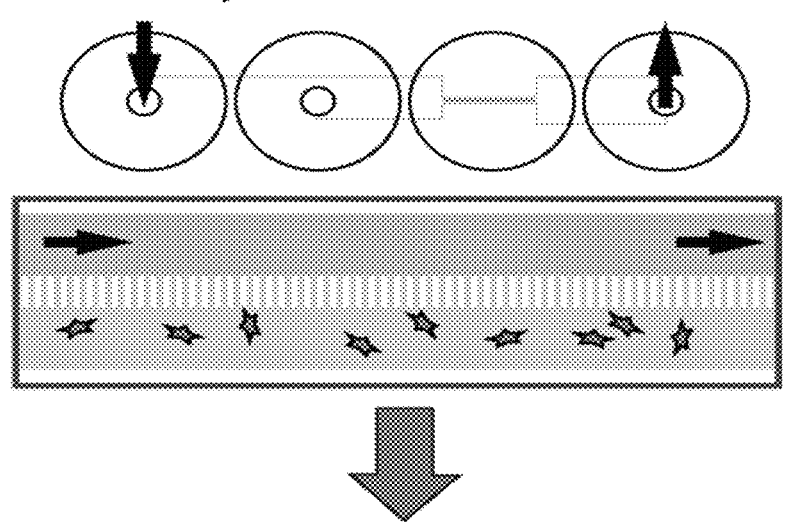
Figure 4C:
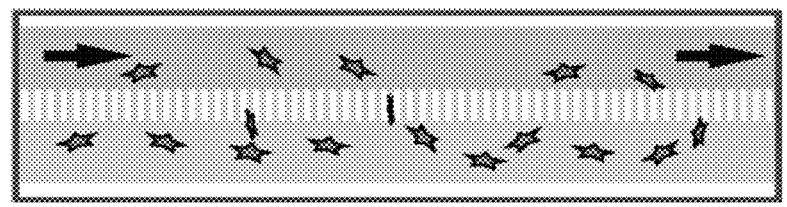

FIGS. 4A-4C are a set of schematics illustrating an example of invasion plate operation according to specific embodiments. Example operation according to specific embodiments proceeds as follows: (FIG. 4A) cells/gels are loaded by capillary flow or other flow means between the cell/gel inlet well and the outlet well; (FIG. 4B) cells are cultured in the 3D environment with continuous perfusion (e.g., gravity driven in a presently preferred embodiment) from the flow inlet well to the flow outlet; (FIG. 4C) invasive cells respond to the flow by crossing the invasion barrier into the invasion chamber where an assay is performed, e.g. by microscopy. In the schematic flowchart as shown, the assay result is positive in that invasive cells did migrate to the invasion chamber. According to specific embodiments, the invention provides for negative assay results wherein the absence of cells in the invasion area after a suitable culture period indicate that invasion cells were not present in the original sample.

FIGS. 5A-5C are a series of micrographs of regions of the invasion chamber after loading with gel to show invasion assay operation according to specific embodiments of the invention. Matrigel mixed with fluorescent dye (red) was loaded by capillary flow into the loading channel and polymerized at 37 C for 15 minutes. FIG. 5A illustrates 40× magnification of the invasion chamber showing the gel fills the loading channel, invasion barriers, and part of the invasion chamber. FIG. 5B shows 200× magnification of the invasion barriers. The polymerized gel can be seen inside the invasion barriers, as well as in the invasion chamber. FIG. 5C shows 200× magnification of the perfusion barrier, showing the gel is unable to cross the narrow channel network. As will be further understood from the teachings herein, the "gel" can have various viscosities down to a fluid viscosity in specific embodiments and specific tests. In specific embodiments, the perfusion barrier allows for use of a wider range of gel viscosities according to the invention.

Figure 6A:
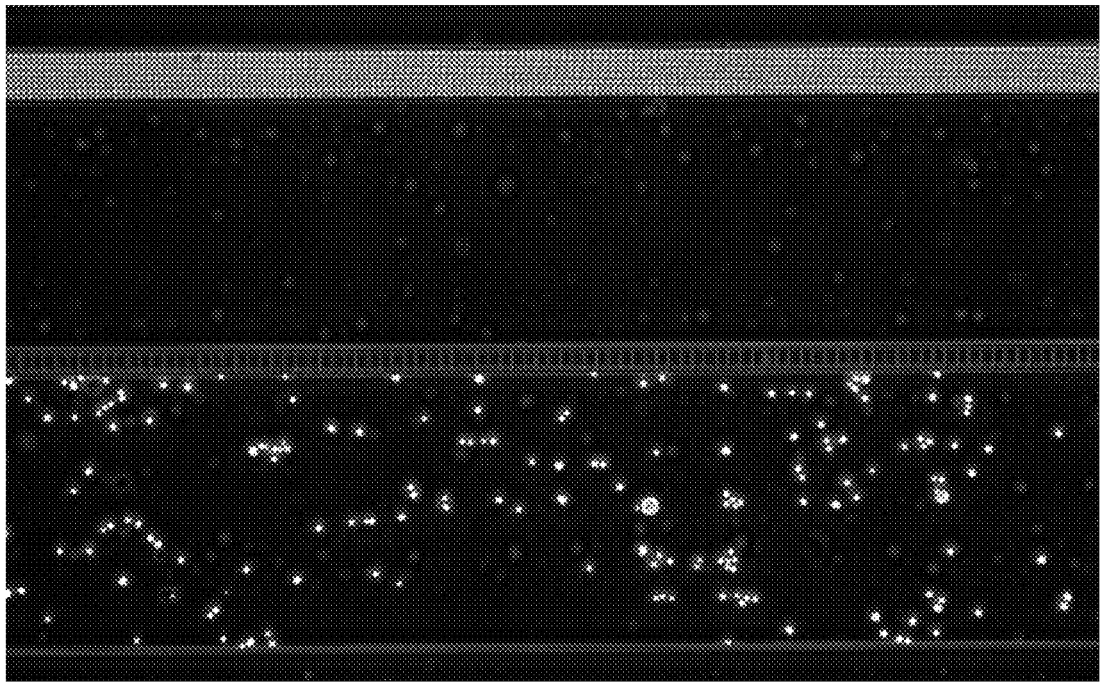
FIGS. 6A-6B are micrographs showing cancer cell invasion in an assay system and device according to specific embodiments of the invention.
Figure 6B:
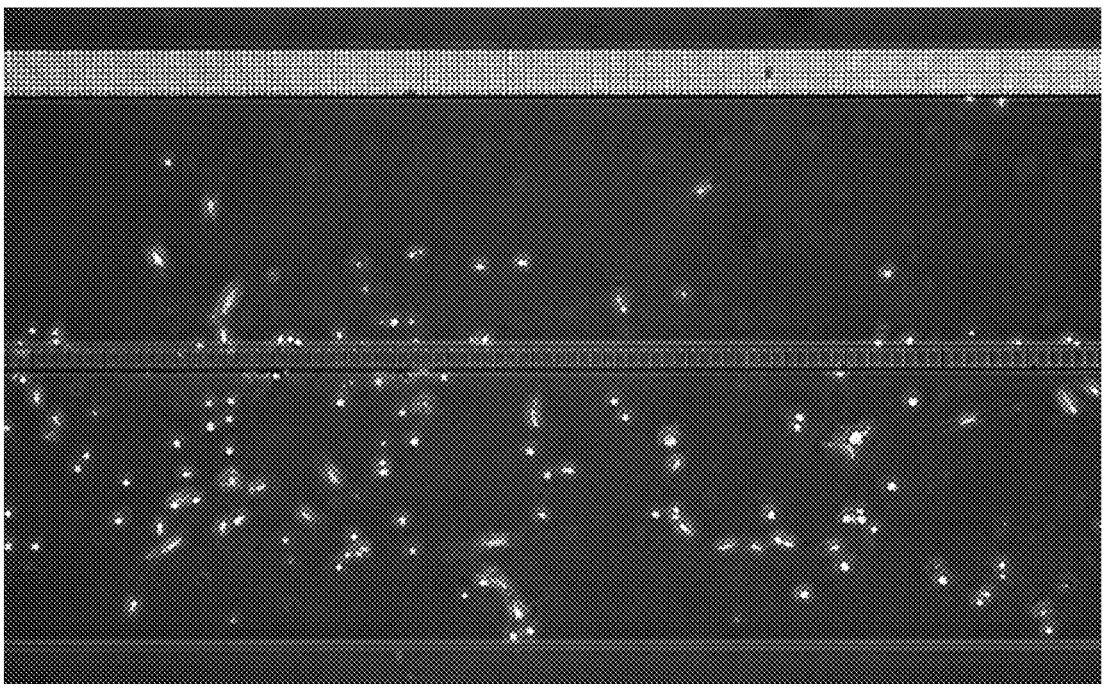

FIGS. 6A-6B are micrographs showing cancer cell invasion in an assay system and device according to specific embodiments of the invention. In this example, HT-1080 invasive human breast cancer cells were loaded in 3D Matrigel and perfused with medium containing 10% serum. FIG. 6A shows cells immediately after loading and polymerization of the gel are located on the bottom side of the invasion barrier. FIG. 6B shows cells after 24 hours of perfusion culture with serum containing medium (known signal for HT-1080 invasion), some of the cells have migrated through the Matrigel and invasion barriers to occupy the invasion chamber. Images taken with phase contrast at 40× magnification.

In further embodiments, various strategies can be used to remove some of all of the cells in the invasion chamber for further analysis. According to specific embodiments, the invention further facilitates this by providing a culture environment in the invasion chamber that sustains the cells until they are removed.

6. Alternative Embodiments

Figure 7A:
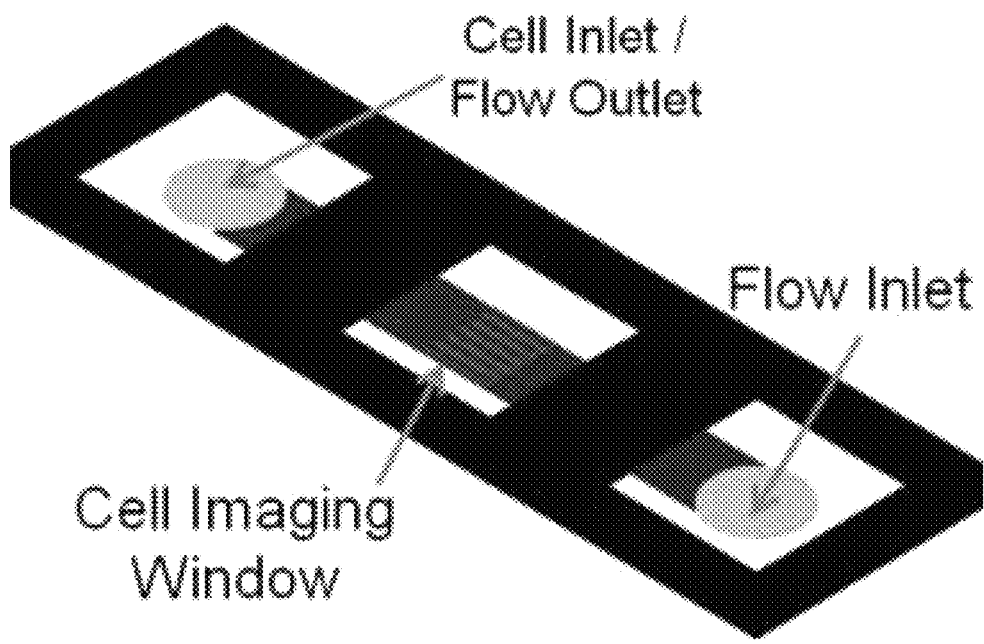
FIGS. 7A-7B are simplified schematic diagrams illustrating in three dimensions the components of a multi-well microfluidic system including a representation of the well frame according to specific embodiments of the invention.
Figure 7B:
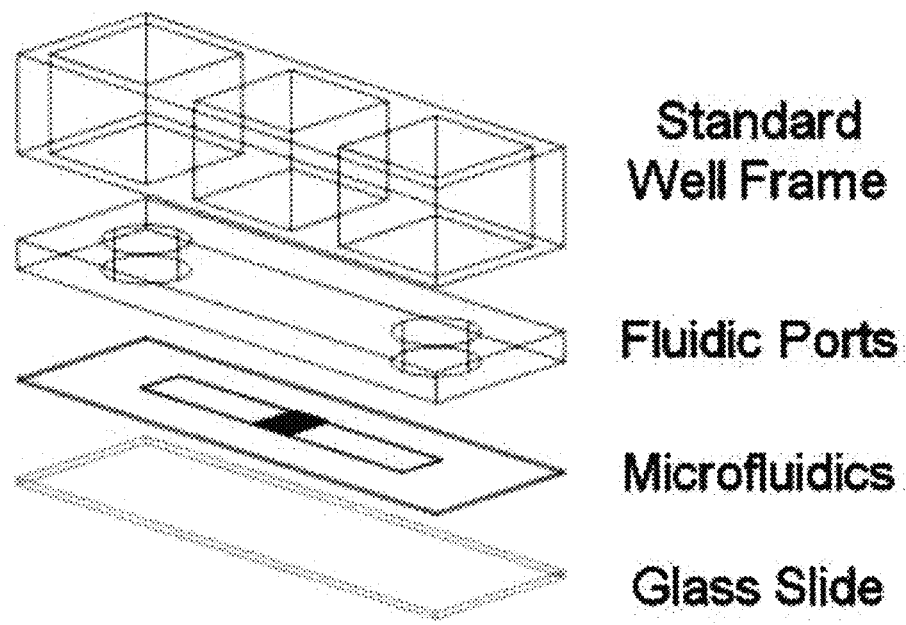
Figure 8:
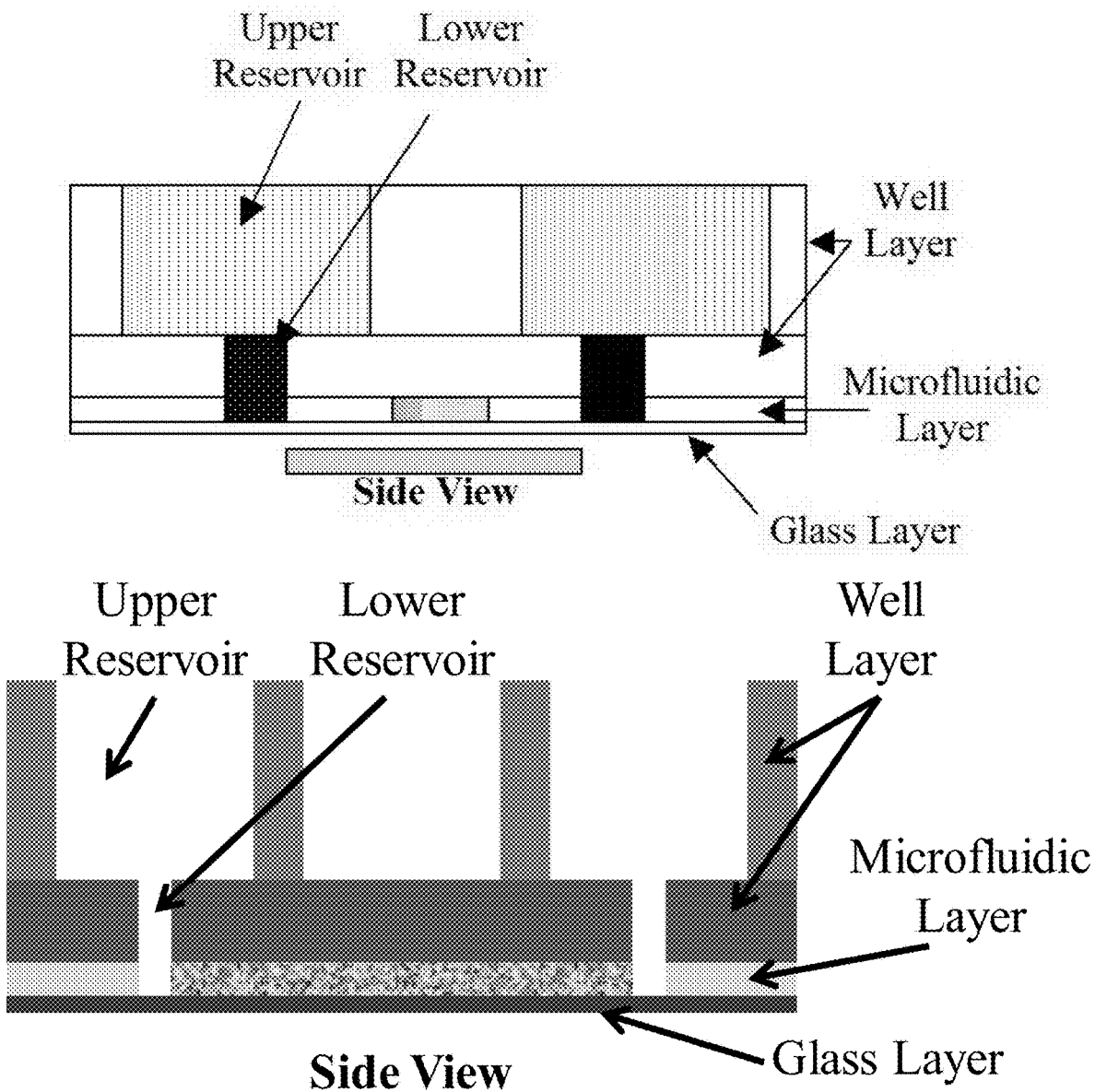
FIG. 8 is a simplified side view showing the general structure of microfluidic culture devices according to specific embodiments of the invention.

A number of other embodiments of the invention are possible. For example, an invasion assay system can take 3 culture wells, rather than 4, by combining for example, one for use as a medium inlet, one for use as a cell inlet/medium outlet, and one for use for cell invasion imaging (which appears as a dark rectangle in the wells in the figure) and/or for providing air passages to a cell culture area. As above, in specific embodiments, each unit can be used as an independent biomimetic device for cell invasion assay. This example is shown for discussion purposes, and any number of other configurations are possible including configurations are described and illustrated in this application or as would be understood or suggested to one of skill in the art having benefit of the teachings provided herein. FIGS. 7A-7B are simplified schematic diagrams illustrating in three dimensions the components of a multi-well microfluidic system including a representation of the well frame according to specific embodiments of the invention. The figure shows a representation of an example 3D construction of a 3-well culture/invasion unit, though 4-well units are presently preferred embodiments. In this example, the flow channel, perfusion barrier, and invasion chamber are located in the microfluidics layer at the imaging window. FIG. 8 is a simplified side view showing the general structure of microfluidic culture devices according to specific embodiments of the invention In further embodiments, air diffusion through the material that defines the microfluidic channels (such as silicone elastomer polydime-thylsiloxane (PDMS)) structure into the culture areas can be facilitated by air passages and air holes as described elsewhere herein.

As discussed elsewhere, various modifications may be made to the cell culture area as described above. Various configurations are possible for the perfusion barrier such as a grid-like passage structure. Other variations will be suggested to those of skill in the art having the teachings provided herein.

The structures disclosed above can also be adapted to systems using more or fewer wells on a standard microtiter well plate or a fully customized or partially customized plate, such as those described in referenced documents and in other examples herein.

Plates and systems as described herein can be used with other configurations of cell culture areas and invasion chambers and micro-fluidic flow structures as described in above referenced patent applications. In one modified design, the cell culture area provided is an essentially rectangular cell culture chamber. The cell culture chamber has cell inlet and outlet passages at the right, and flow outlets also at the right.

In this example, the cell passages are paired, with the center pair used for cell flow loading and the pairs on either side used as a cell flow outlet.

Once the cells are loaded, the invasion assay proceeds as outlined above, after any invasive cells have had sufficient time to move through the invasion barrier.

Figure 9A:
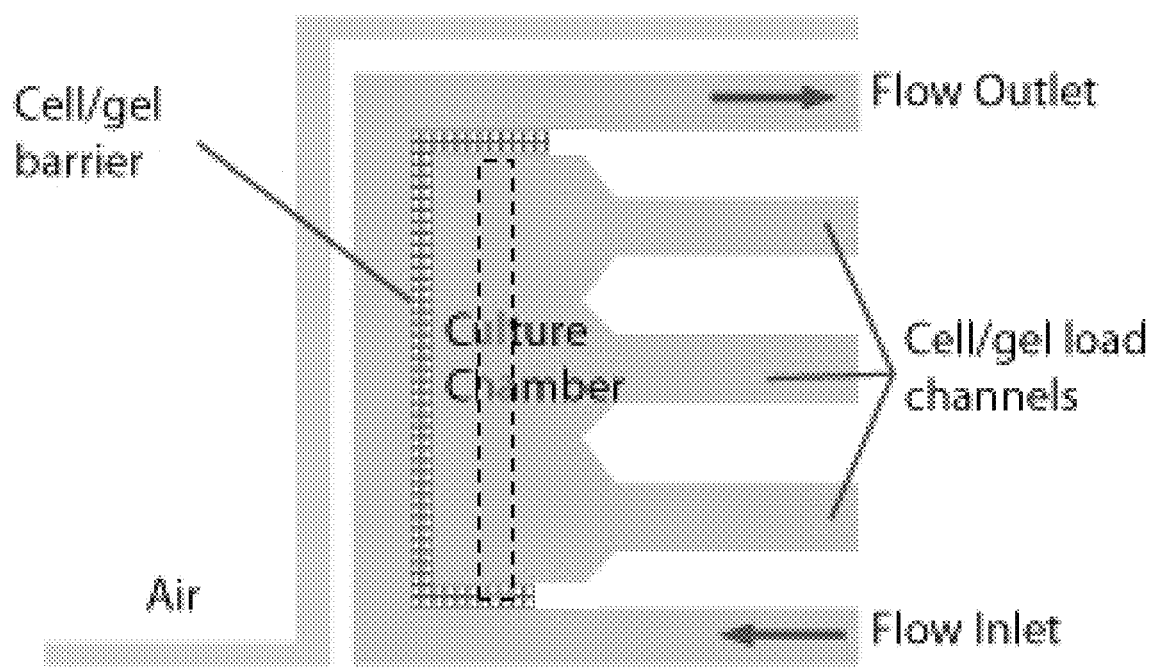
FIGS. 9A-9B illustrate configuration and operation of an example cell culture chamber design for 3D gel cell culture according to specific embodiments of the invention.
Figure 9B:
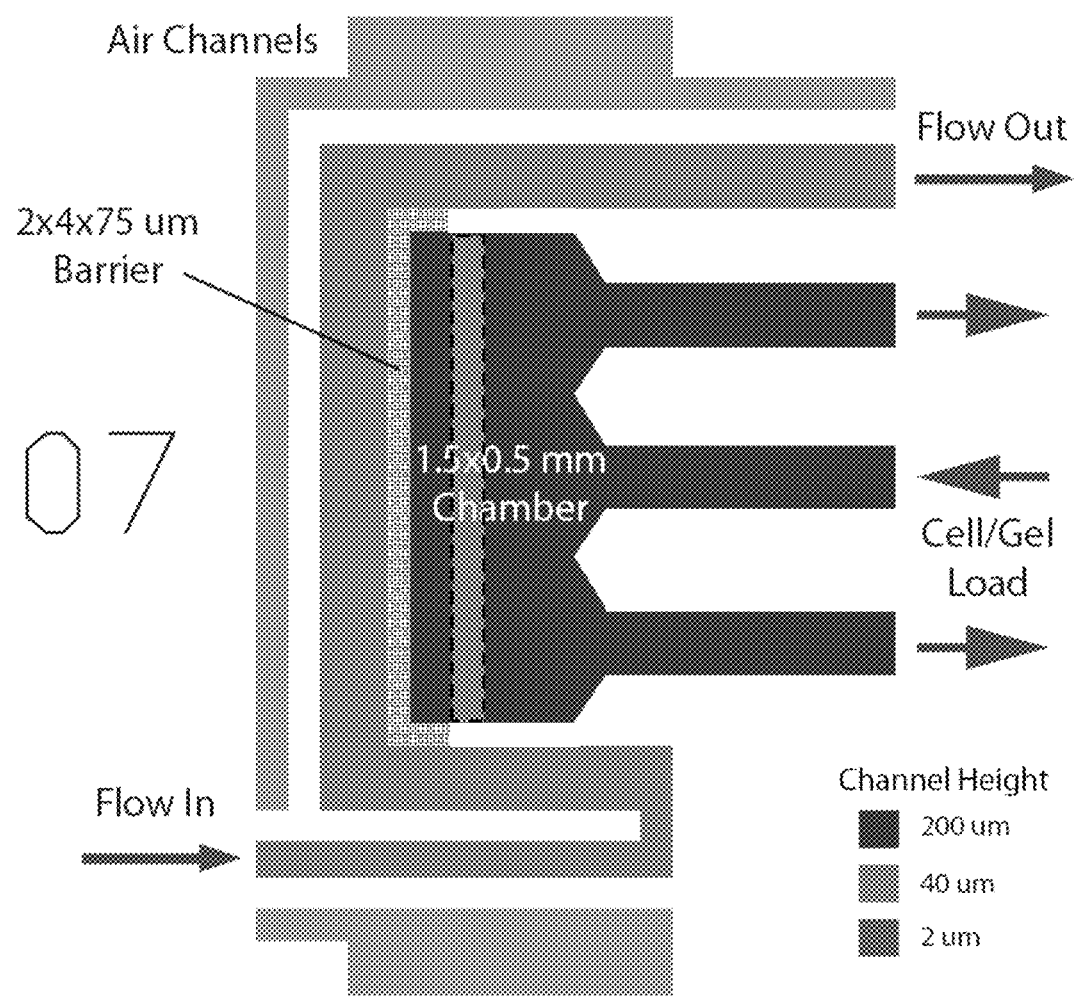

FIGS. 9A-9B illustrate configuration and operation of an example cell culture chamber design for 3D gel cell culture according to specific embodiments of the invention. This example includes a cell/gel perfusion barrier with a cross-hatch perfusion passage design and an invasion barrier as discussed above. The cross hatch design allows cells in a gel matrix to be flowed into the chamber and allows for perfusion of media. While the cross-hatch perfusion barrier is presently preferred in some designs, culture chambers with different perfusion barriers or no perfusion barriers are also implemented according to specific embodiments. A flow around channel for media includes an outlet and inlet both on the same side of the barrier. FIG. 9A illustrates a general embodiment where the outlet and inlet openings are shown to the right. FIG. 9B illustrates an inlet channel to the left and outlet channel to the right, which configuration is better suited in some example systems using a well plate as described herein. This figure also provides detailed example dimensions of a sample design according to specific embodiments of the invention. Thus, in a further embodiment, a cell culture chamber is modified to allow easier culture of cells in 3D gel matrix. In this design, a perfusion barrier separates the cell culture area and the flow channel as illustrated. The barrier is designed to retain a 3D gel in the culture chamber. Coupling the barrier with the 3-channel cell/gel inlet design described above is an important feature that provides improved performance. By having separate flow inlets/outlets on each side of the barrier, it is possible to localize a fluid gel in the culture chamber, and not have it obstruct the flow channel.

An invasion barrier as described above is placed in the region indicated by the dashed line in the figure and is used to separate the cell entry and culture chamber from the invasion chamber, as will be understood from the teachings herein. In alternative embodiments, perfusion channels may be provided so that they are only adjacent to the invasion chamber.

As discussed elsewhere, in specific embodiments, the invention provides a 3D gel environment for biologic cell culture and invasion assays, for example using a temperature sensitive gel culture matrix, such as Matrigel™, Geltrex™, collagen, etc. An example gel is liquid at 4 C, which, for example polymerizes at room temperature or 37 C. In one example method, cells are initially mixed with a cell suspension on ice. The solution is then pipetted into the cell inlet well, and carried into the microfluidic chambers and the culture and invasion chambers via capillary flow. In specific examples, the plate is kept at room temperature. The flow rate allows sufficient cell/gel solution to fully fill the culture chamber prior to polymerization while the cells do not enter the invasion chamber during fluid flow because of the size of the invasion passages. The perfusion barrier prevents any of the gel solution from leaking into the flow channel. As the gel warms up, it polymerizes into a semi-solid mass, with cells embedded in the culture region. Flow of media in the flow channel diffuses into the cell culture chamber through the invasion chamber and through the gel and nourishes the cells for culture while providing an attractant for invasive cells to move through the invasion barrier to the invasion chamber. This novel design allows the invention to provide a 3D gel culture system in a microfluidic device while avoiding the problem of having gel block the flow channels.

In the example shown in FIG. 9B, the blue areas indicate air flow, and are optional and not present in all embodiments. The grey areas indicate a fluid channel, with an example height of around 40 μm, the red area indicates cell culture and invasion areas, with an example height of around 200 μm, and the green area indicates a perfusion barrier with an example height of around 2 μm. The yellow invasion barrier will generally have the same height or similar height as the culture areas (e.g., 200 μm), but will have invasion barrier structures as described above.

Once the cells are loaded, the invasion assay proceeds as outlined above, after any invasive cells have had sufficient time to move through the invasion barrier.

3D Gel System

In one example system, referred to at times herein as the 3D:M, multiplexed perfusion imaging of cells can be performed in a 3D gel matrix. An example plate contains 24 independent culture units that can be loaded with cells/gel as a user chooses. In an example system, each row of the plate (A-H) contains 3 fully independent flow units (4 wells each), consisting of a medium inlet (e.g., cols. 1, 5, 9), a cell culture/invasion/imaging well (e.g., cols. 2, 6, 10), cell/gel inlet (cols. 3, 7, 10), and an outlet (cols 4, 8, 12). Air diffusion channels (blue) provide gas transfer to the cells. The inlets are designed to allow continuous flow of culture media to the cells at 40 μl/day via a gravity driven process. In this example, each chamber is 1.5×0.5 mm in size, with a height of 200 μm. The perfusion barrier ensures uniform nutrient transfer through the gel matrix and a thin cover glass bottom (170 μm) allows for optimum image quality. An invasion barrier provides separation between a culture region and an invasion region. 3D gel loading in such a system can be performed as described above and in incorporated references.

As discussed elsewhere herein, any of the various novel microfluidic cell culture chambers and associated microfluidic structures can, according to specific embodiments of the invention, be integrated with a well titer plate device as is commonly used in macro cell culturing assays. A number of specific examples are provided below, though the invention encompasses other systems for integrating with the microfluidic devices.

In this design, each culture unit consists of 4 well positions. The first well is for perfusion medium, the second well is for cell inlet, the third well is for imaging the microfluidic chamber, and the fourth well is the outlet. A cell barrier/perfusion channel localizes cells to the cell area and improves nutrient transport during continuous perfusion culture. The low fluidic resistance of the cell inlet to outlet path enables cells to be rapidly loaded via gravity or surface tension methods without an external cell loading mechanism. The high fluidic resistance of the perfusion inlet flow channels allows long term continuous perfusion of medium via gravity flow without any external pump mechanism. An invasion barrier operates to separated cultured cells from an invasion region for invasion assays.

Figure 10A:
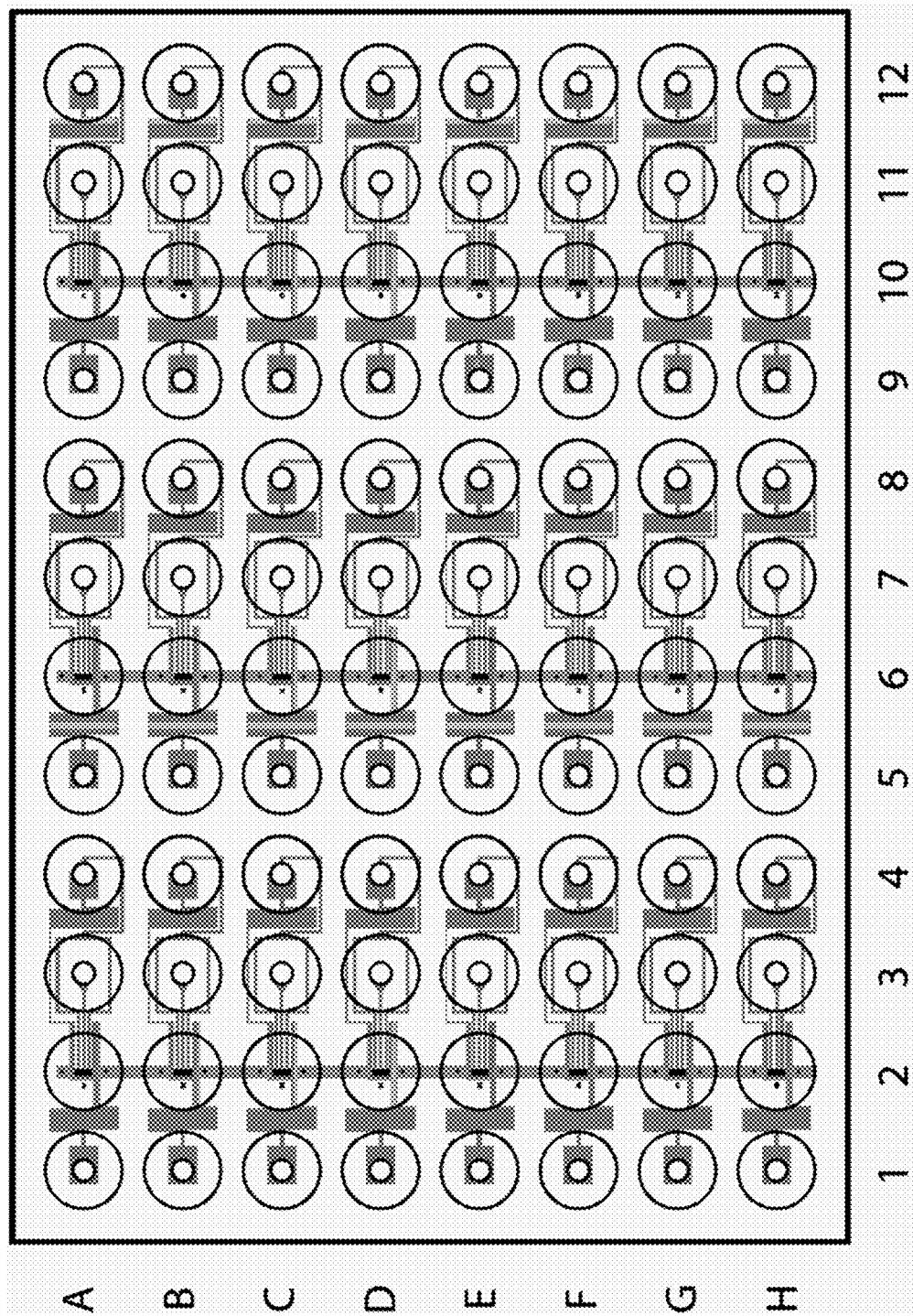
FIGS. 10A-10C illustrate a 24 unit "3D culture" plate on a 96 well plate according to specific embodiments of the invention.
Figure 10B:
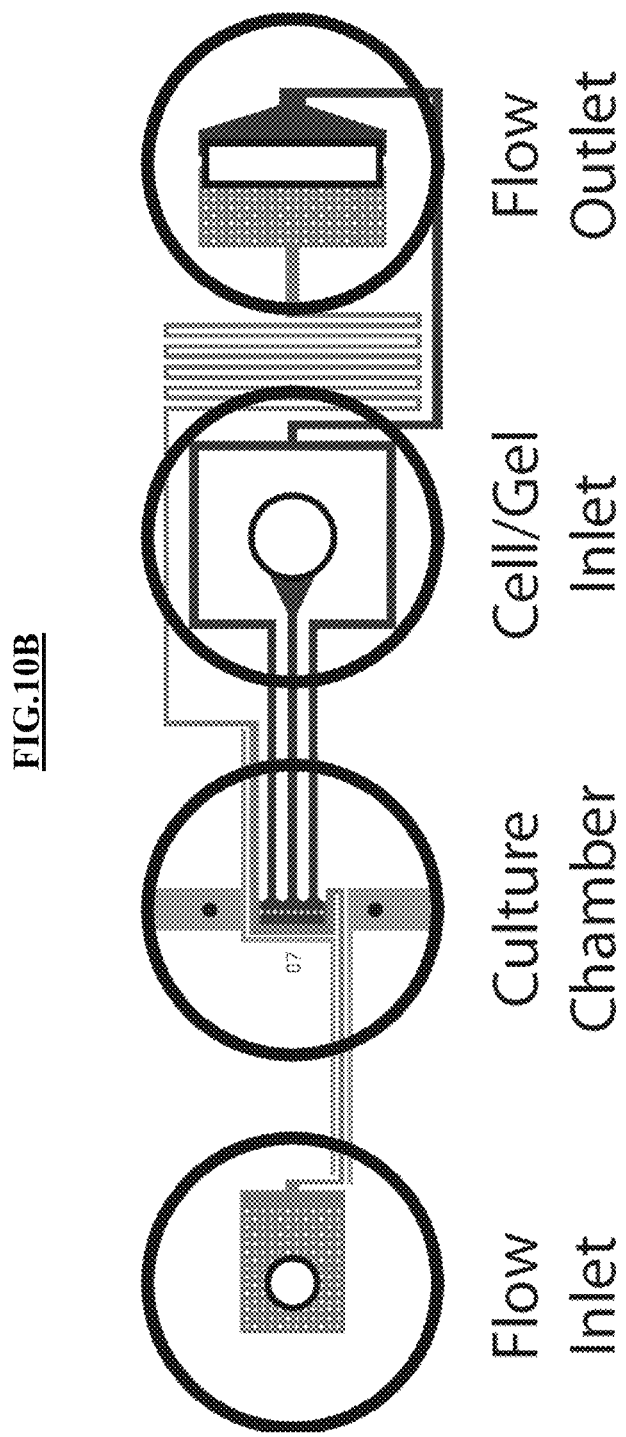
Figure 10C:
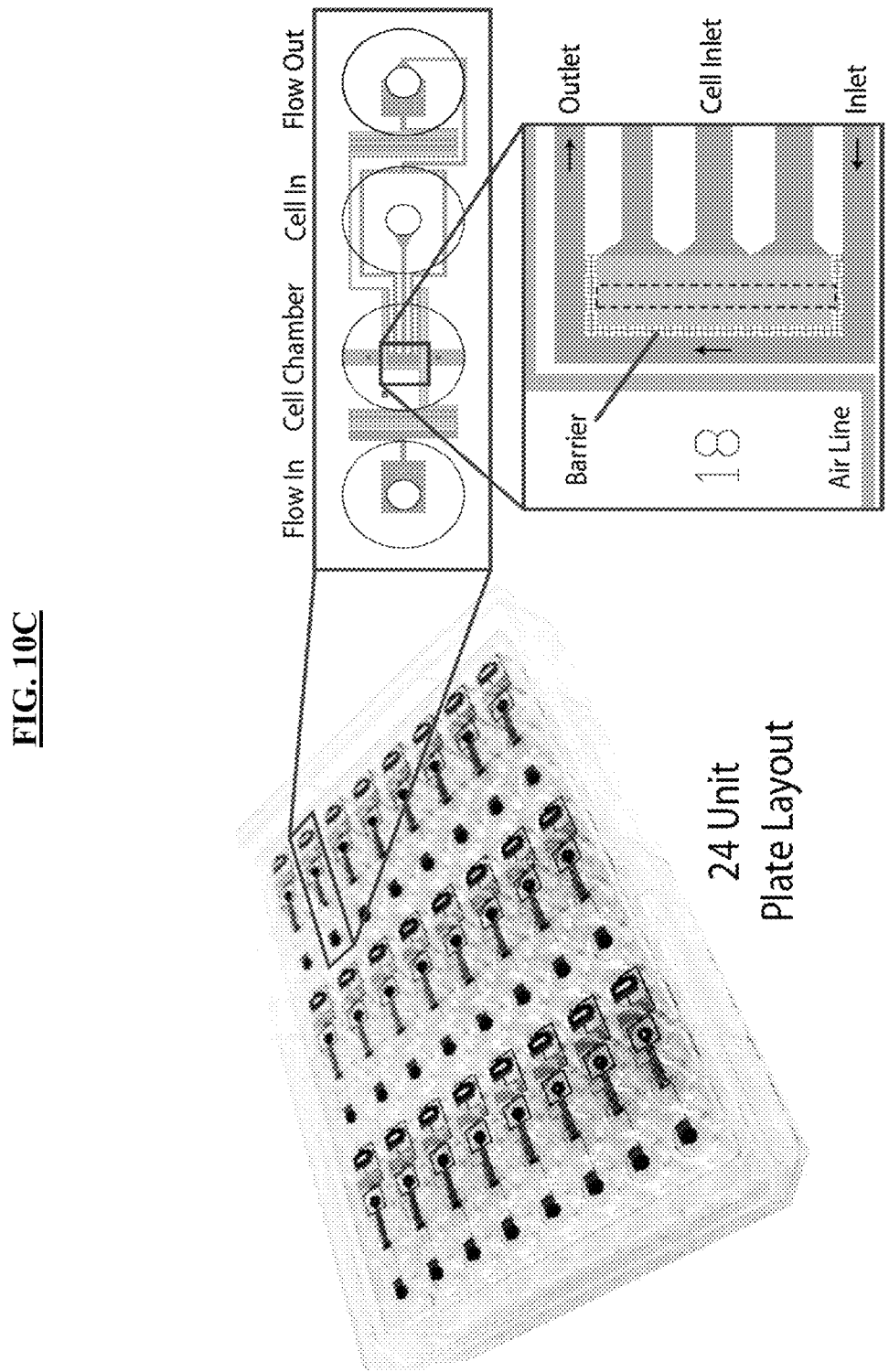

FIGS. 10A-10C illustrate a 24 unit "3D culture" plate on a 96 well plate according to specific embodiments of the invention. According to specific embodiments of the invention, this configuration is a designed for high-thru-put production work. The design allows cells to be cultured in various 3D gel matrix media with continuous perfusion medium exposure for long term cell assay and cell imaging experiments. In a specific embodiment, using a standard 96-well format and passive gravity driven perfusion allows simple integration with existing laboratory equipment.

In a specific example, a 96-well plate contains 24 independent 3D culture units with microfluidic channels (which are stained in the Figure for visibility) A single unit with flow channels stained is shown in FIG. 10C. In an example operation, media flows from the inlet well past the cultured cells and collects in the outlet well. Cells and gel are loaded by the user into the biomimetic cell culture chamber.

In an example specific system, the cell chamber is designed to mimic the interstitial tissue environment, with cells embedded or overlayed in physiologic extracellular matrix (ECM), and fed via diffusion from a continuously perfused capillary channel. The cell microenvironment enables long term growth in, e.g., a 200 micron thick gel layer. Oxygenation channels maintain adequate gas transport, and the glass coverslide bottom allows high quality cell imaging. The standard layout allows the advanced microfluidic units to be operated just like a typical 96-well plate. The gravity driven perfusion design eliminates the need for pump or tubing connections, as described above.

In an example system, an expected number of cells per unit is about 500 cells. An example perfusion rate is 40 ul/day for a single unit. The cell chamber volume is 150 nL, and the chamber dimensions are 1.5×0.5×0.2 mm. The gas diffusion membrane is 50 um silicone with a bottom surface #1.5 thickness coverglass.

An open top microfluidic cell culture chamber for continuous perfusion can also be modified with a second barrier separating an invasion region from a culture region.

7. Pneumatic Manifold

While gravity or passive loading is effective for some microfluidic cell culture devices and desirable in some embodiments, a proprietary pneumatic manifold, as described herein and in the above referenced applications may be mated to the plate and pneumatic pressure is applied to the cell inlet area for cell loading and for culturing during invasion assays.

Figure 11A:
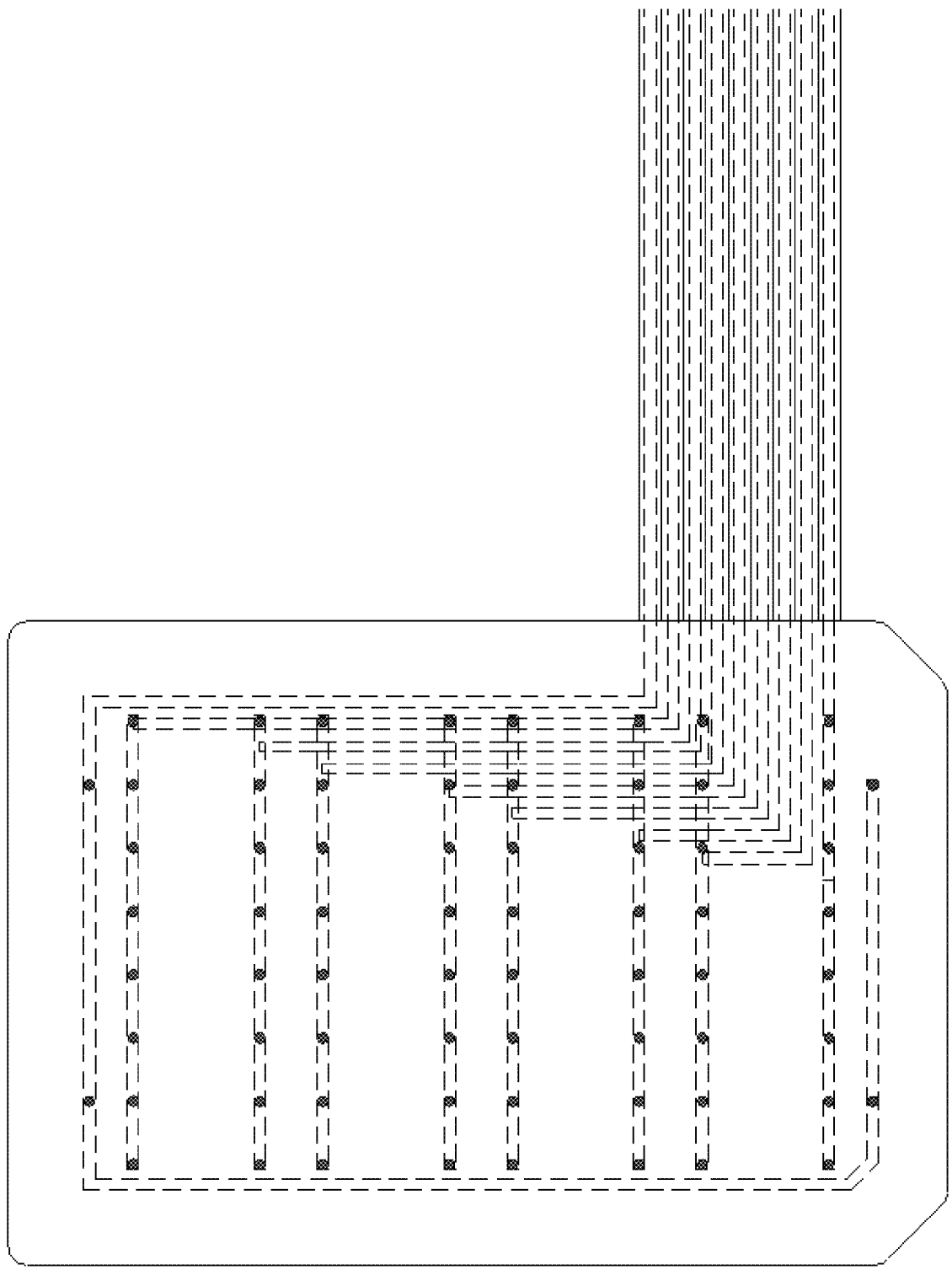
FIGS. 11A-11C shows a top view, side view, and plan view of a schematic of an example manifold according to specific embodiments of the invention. In this example, the eight tubing lines to the right are for compressed air, and each is configured to provide pressure to a column of cell inlet wells in a microfluidic array. The left-most line in the figure is for vacuum and connects to an outer vacuum ring around the manifold. Each column of wells is generally connected to a single pressure line with wells above imaging regions skipped.
Figure 11B:
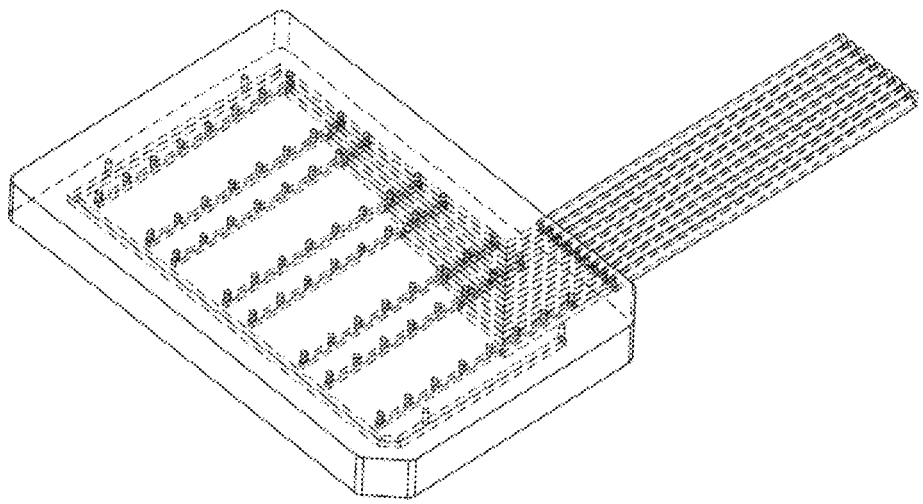
Figure 11C:
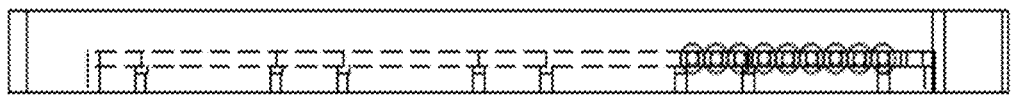

FIGS. 11A-11C shows a top view, side view, and plan view of a schematic of an example manifold according to specific embodiments of the invention. In this example, the eight tubing lines to the right are for compressed air, and each is configured to provide pressure to a column of cell inlet wells in a microfluidic array. The left-most line in the figure is for vacuum and connects to an outer vacuum ring around the manifold. Each column of wells is generally connected to a single pressure line with wells above imaging regions skipped. The manifold is placed on top of a standard well plate or other configuration of plate. A rubber gasket lies between the plate and manifold, with holes matching the manifold (not shown). The vacuum line creates a vacuum in the cavities between the wells, holding the plate and manifold together. Pressure is applied to the wells to drive liquid into the microfluidic channels (not shown). A typical pressure of 1 psi is used, therefore the vacuum strength is sufficient to maintain an air-tight seal. In one example there are 9 tubing lines to the pressure controller: 8 lines are for compressed air and 1 line is for vacuum (leftmost). In specific example embodiments, each column is connected to a single pressure line. Columns above the cell imaging regions are skipped.

Pressurized cell loading in a system according to specific embodiments of the invention has been found to be particularly effective in preparing cultures of aggregating cells (e.g., solid tumor, liver, muscle, etc.). Pressurized cell loading also allows structures with elongated culture regions to be effectively loaded. Use of a pressurized manifold for cell loading and passive flow for perfusion operations and invasion assay allows the invention to utilize a fairly simple two inlet design, without the need for additional inlet wells and/or valves as used in other designs.

In a further embodiment, a plate manifold includes an additional "gas line" that is used to bathe the cells in the microfluidic device with a specified gas environment (for example, 5% $CO_2$). Other examples include oxygen and nitrogen control, but any gaseous mixture can be sent to the cells. The gas flows through the manifold into the sealed wells above the cell culture area and holes in the microfluidic device enable the gas to flow into specified microfluidic air channels, as described above. The gas permeable device layer (PDMS) allows the gas to diffuse into the culture medium prior to exposing the cells. By continuously flowing the gas through the microfluidic plate, a stable gas environment is maintained.

This provides an optional means for controlling the gas environment to placing the microfluidic plate into an incubator. In this modified manifold, the manifold can be used to create a "micro-incubator" independent of the ambient air.

Figure 12:
FIG. 12 illustrates an example system and manifold for operating the microfluidic plates according to specific embodiments of the invention.
Figure 13:
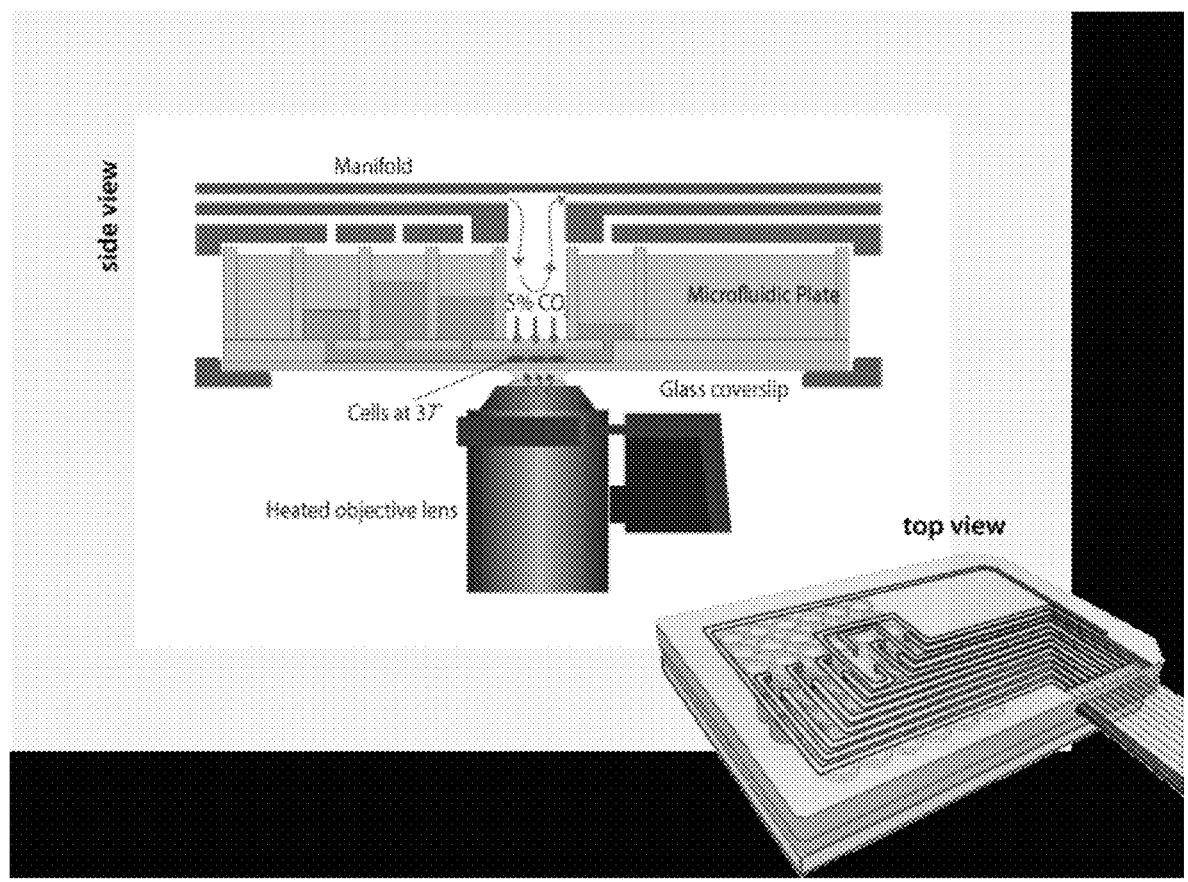
FIG. 13 illustrates a manifold with additional gas line and an objective lens according to specific embodiments of the invention.

FIG. 12 illustrates an example system and manifold for operating the microfluidic plates according to specific embodiments of the invention.

As described in previous applications, the format of the microfluidic plate design allows two automation-friendly flow modalities dependent on the extent of dispensing/aspiration. The first is surface tension mediated flow. In this case, when the lower reservoir is aspirated in either one of the wells, the capillary force of the fluid/air interface along with the wetted surfaces (glass, silicone, acrylic) will rapidly draw liquid in from the opposing well until the lower reservoir is filled (or in equilibrium with the opposing lower reservoir). This effect is useful for microfluidic flows as it is only evident when the reservoir diameter is small and the flow volumes are small. In an example array design, the lower reservoir wells are 1-2 mm in diameter, and with a total flow volume of approximately 3-5 microliters. Since the microfluidic channel volume is only 0.2 microliters, this mechanism is well suited for cell loading and cell exposures.

The second mechanism is gravity driven perfusion, which is well suited for longer term flows, as this is dependent on the liquid level difference and not the reservoir dimensions. According to specific embodiments of the invention, this may be accomplished by adding more liquid into one reservoir (typically filling near the top of the upper reservoir). The fluidic resistance through the microfluidic channels will determine how long (e.g., 24 hours) to reach equilibrium between the wells and thus determine how often wells should be refilled.

Figure 14:
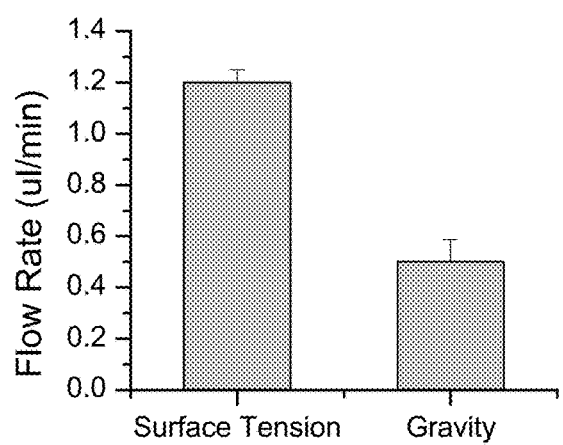
FIG. 14 is a graph illustrating an example of flow rate difference between a surface tension mechanism and a gravity driven mechanism according to specific embodiments of the invention.

FIG. 14 shows the flow rate difference between the surface tension mechanism and the gravity driven mechanism. For the surface tension flow, in an example, 5 microliters was dispensed into the lower reservoir followed by aspiration of the opposing lower reservoir. For the gravity flow, a liquid level difference of 2.5 mm was used, with both wells filled into the upper reservoir portion.

Figure 15:
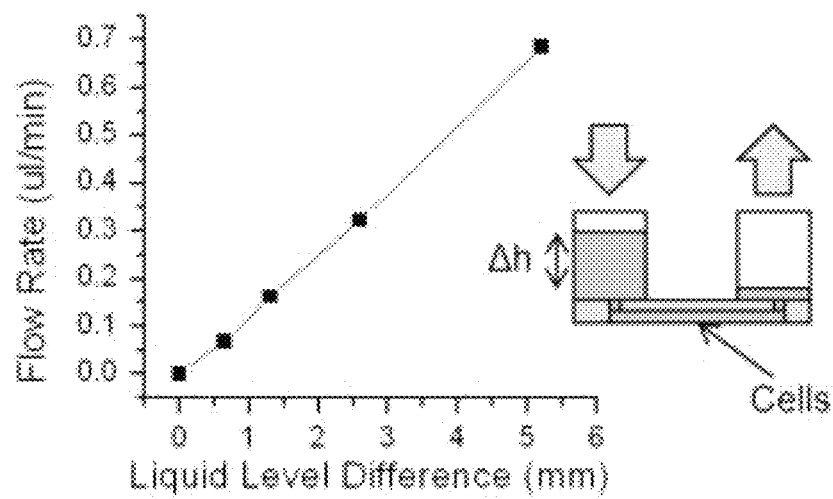
FIG. 15 is a graph illustrating an example of the extent to which gravity perfusion rate is responsive to the liquid level difference between the two upper reservoir wells according to specific embodiments of the invention.

The gravity perfusion rate is also responsive to the liquid level difference between the two upper reservoir wells as illustrated in FIG. 15. This fact allows an automated dispenser/aspirator to control and maintain a given perfusion flow rate over a 10-fold range during culture. Here, different liquid level differences were produced via dispensing volumes and measured for volumetric flow rate.

According to specific embodiments of the invention, the liquid height difference between the inlet/outlet wells across the plate can also be precisely controlled using a mechanical tilting platform. In this implementation, it is possible to maintain a constant flow rate over time, as well as back-and-forth flow with different forward and reverse times (i.e. blood flow).

In an example system, perfusion cell culture can be initiated by filling the flow inlet reservoir with 200-300 microliters of fresh medium (e.g., DMEM supplemented with 10% fetal bovine serum) and aspirating the cell inlet upper reservoir. The liquid level difference between the flow inlet and cell inlet wells will then cause a continuous gravity driven flow through the attached cells. For sustained culture, the flow inlet well is refilled and the cell inlet well aspirated during a period depending on fluidic resistance and reservoir volumes (e.g., every 12, 24, 36, 48, 72 hours).

Cell assay can be performed directly on the microfluidic cell culture using standard optically based reagent kits (e.g. fluorescence, absorbance, luminescence, etc.). For example a cell viability assay utilizing conversion of a substrate to a fluorescent molecule by live cells has been demonstrated (CellTiter Blue reagent by Promega Corporation). The reagent is dispensed into the flow inlet reservoir and exposed to the cells via gravity perfusion over a period of time (e.g., 21 hours). For faster introduction of a reagent or other fluid, the new fluid can be added to the flow inlet reservoir followed by aspiration of the cell inlet reservoir.

Data can be collected directly on the cells/liquid in the microfluidic plate, such as placing the plate into a standard fluorescence plate reader (e.g., Biotek Instruments Synergy 2 model). In some reactions, the substrate may diffuse into the outlet medium, and therefore be easily detected in the cell inlet reservoir. For cell imaging assays, the plate can be placed on a scanning microscope or high content system. For example, an automated Olympus IX71 inverted microscope station can be used to capture viability of cultured liver cells with a 20× objective lens.

By repeatedly filling/aspirating the wells, cells can be maintained for long periods of time with minimal effort (e.g. compared to standard "bioreactors" which require extensive sterile preparation of large fluid reservoirs that cannot be easily swapped out during operation).

Automated Systems

Figure 16:
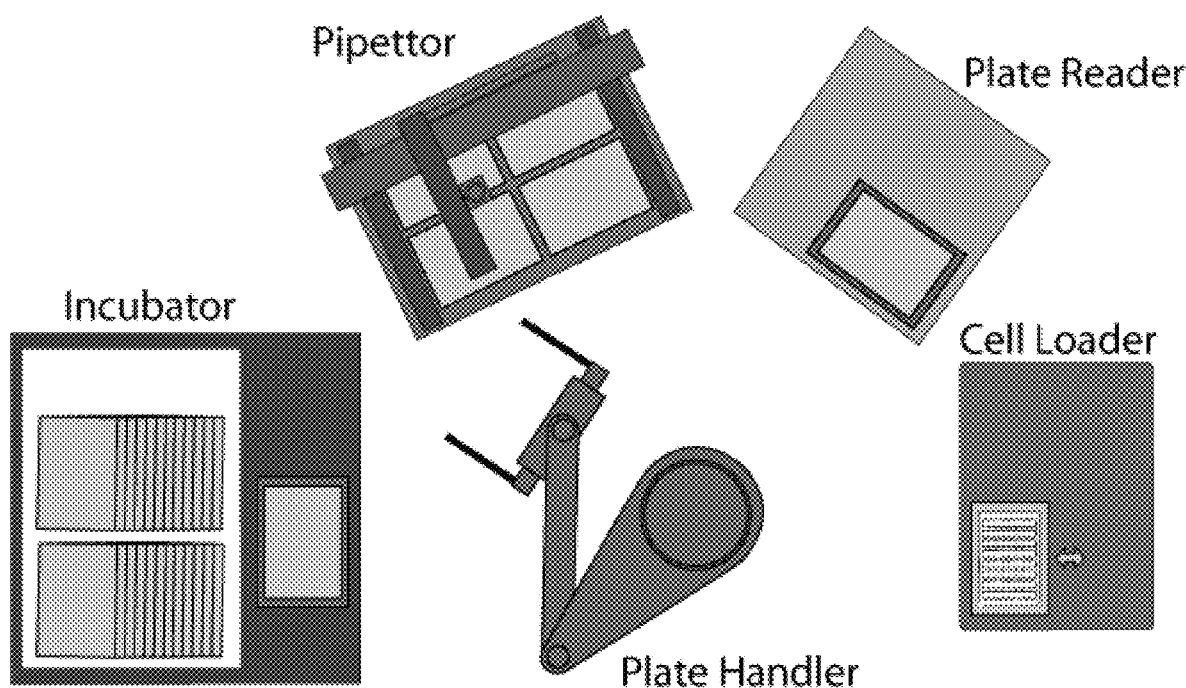
FIG. 16 illustrates a top view schematic of an example cell culture automation system according to specific embodiments of the invention.

FIG. 16 illustrates a top view schematic of an example cell culture automation system according to specific embodiments of the invention. Because the plates are designed to be handled using SBS compliant instruments, various "off-the-shelf" machines can be used to create an automated system. This schematic shows an example of how this is accomplished. A robotic arm (plate handler) moves the microfluidic plates from station to station. An automated incubator stores the plates at the proper temperature and gas environment for long term perfusion via gravity flow. The pipettor dispenses liquids (media, drugs, assay reagents, etc.) to the inlet wells and removes liquid from the outlet wells. A plate reader is used for assay. The cell loader is optionally used to introduce the cells to the microfluidic arrays at the beginning of the experiment. The cell loader in particular is generally not "off-the-shelf" and operates by applying pneumatic pressure to specified wells of the array plate to induce flow. Standard or custom computer software is available to integrate operations.

The basic process includes: 1) removing the plate from the incubator, 2) removing liquid from the outlet wells via the pipettor, 3) moving a media/drug storage plate from the "plate stacks," 4) transferring liquid from the media/drug plate to the microfluidic plate via the pipettor, 5) placing the microfluidic plate into the incubator, 6) repeat for each plate, 7) repeat after specified time interval (e.g. 24 hours).

The 96-well plate standard allows the microfluidic system to be operated using standard techniques and equipment. For example, liquid dispensing is achieved with standard pipette mechanics, and cell culture and analysis is compatible with existing incubators and plate readers. A custom built cell loading system can be used to load the cells using air pressure as described above. The gravity driven flow culture configuration utilizes the medium level difference between the inlet and outlet well as well as engineering the fluidic resistances to achieve the desirable flow rate in nL/min regime. This provides the significant advantage of being able to "passively" flow culture medium for long periods of time (for example, up to 4 days) without the use of bulky external pumps.

Integrated Systems

Integrated systems for the collection and analysis of cellular and other data as well as for the compilation, storage and access of the databases of the invention, typically include a digital computer with software including an instruction set for sequence searching and/or analysis, and, optionally, one or more of high-throughput sample control software, image analysis software, collected data interpretation software, a robotic control armature for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system further comprises valves, concentration gradients, fluidic multiplexors and/or other microfluidic structures for interfacing to a microchamber as described.

Readily available computational hardware resources using standard operating systems can be employed and modified according to the teachings provided herein, e.g., a PC (Intel x86 or Pentium chip-compatible DOS,™ OS2,™ WINDOWS,™ WINDOWS NT,™ WINDOWS95,™ WINDOWS98,™ LINUX, or even Macintosh, Sun or PCs will suffice) for use in the integrated systems of the invention. Current art in software technology is adequate to allow implementation of the methods taught herein on a computer system. Thus, in specific embodiments, the present invention can comprise a set of logic instructions (either software, or hardware encoded instructions) for performing one or more of the methods as taught herein. For example, software for providing the data and/or statistical analysis can be constructed by one of skill using a standard programming language such as Visual Basic, Fortran, Basic, Java, or the like. Such software can also be constructed utilizing a variety of statistical programming languages, toolkits, or libraries.

FIG. 17 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

Various programming methods and algorithms, including genetic algorithms and neural networks, can be used to perform aspects of the data collection, correlation, and storage functions, as well as other desirable functions, as described herein. In addition, digital or analog systems such as digital or analog computer systems can control a variety of other functions such as the display and/or control of input and output files. Software for performing the electrical analysis methods of the invention are also included in the computer systems of the invention.

Other Embodiments

Although the present invention has been described in terms of various specific embodiments, it is not intended that the invention be limited to these embodiments. Modification within the spirit of the invention will be apparent to those skilled in the art.

It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this submission, including any references filed as part of an Information Disclosure Statement, are incorporated by reference in their entirety.

What is claimed:

1. A microfluidic system comprising:
a multi well plate, comprising a first well used as a flow inlet, a second well used as an invasion chamber, and a third well used as both a cell/gel inlet and a flow outlet;
a cell/gel loading channel in communication with the third well and passing under the second well;
a flow channel in communication with the first well, passing under the second well and terminating at the third well;
a microfluidic device comprising a plurality of microstructures, the plurality of microstructures comprising:
a substantially linear invasion barrier in contact with the cell/gel loading channel and defining a single side of an invasion chamber, the invasion barrier separating the cell/gel loading channel from the invasion chamber, the invasion barrier allowing passage of gel and invasive cells into the invasion chamber; and
a substantially linear perfusion barrier separating the invasion chamber from the flow channel, the perfusion barrier defining a single side of the invasion chamber opposite from the invasion barrier, the perfusion barrier configured to retain the cell/gel mixture only within the invasion chamber and the cell/gel loading channel so that the cell/gel mixture does not enter the flow channel, wherein the flow channel is configured to provide a source of liquid media for feeding cells that are present in the cell/gel loading channel or the invasion chamber or both;
wherein said invasion chamber comprises a rectangular region disposed between said invasion barrier and said perfusion barrier, such that said perfusion barrier and said invasion barrier form two opposite parallel sides of said rectangular region, and
further wherein the microfluidic device is small enough to fit within a diameter of the second well in the multiple well plate, said diameter being about 7 millimeters or less.

2. The system of claim 1 wherein:
the invasion barrier comprises a first set of channels, and the perfusion barrier comprises a second set of channels.

3. The system of claim 1 where the microfluidic device is positioned such that it is operational and viewable through the invasion chamber.

4. The system of claim 2 wherein the first set of channels allows passage of invasive cells and the second set of channels does not.

5. The system of claim 1 configured such that flow from the flow inlet to the flow outlet is driven by a gravity flow, defined as a flow arising from a liquid height difference between the first well and the third well.

6. The system of claim 2 further wherein:
the first set of channels have dimensions of about 50×8×8 μm in length, width, and height or about 25-100 μm, 4-12 μm, 4-12 μm in length, width, and height; and
the second set of channels have dimensions of about 2 μm or a minimum dimension of about 0.5-4 μm in height or width or both.

7. The system of claim 2 configured such that an invasion assay may be performed by enumerating a number of cells in the invasion chamber relative to a number of cells in the cell/gel loading channel at one or more time points.

8. The system of claim 1:
wherein the multi wall plate is a standard N-well plate, where N equals any standard culture well plate, including 48, 96, 192, 384 well plates.

9. The system of claim 2 further wherein:
the second set of channels are narrower than cells to be cultured, such that cells cannot pass therethrough; and
the first set of channels are narrower than passive cells but wide enough to allow cell invasion.

10. The microfluidic system of claim 1, wherein a cell/gel mixture is loaded into the third well.

11. The microfluidic system of claim 10, wherein the cell/gel mixture comprises normal cells and invasive cells.

12. The microfluidic system of claim 1, wherein the first well, the second well and the third well are arranged linearly.

13. A method of culturing cells comprising:
placing media in a first well of a multi well plate, wherein a flow channel is in communication with the first well, passes under a second well of the multi well plate and terminates at a third well of the multi well plate;
placing a cell/gel mixture in third well of the multi well plate, wherein a cell/gel loading channel is in communication with the third well, and passes under the second well;
providing an invasion chamber at the second well, where a substantially linear invasion barrier is in contact with the cell/gel loading channel, defines one side of the invasion chamber, separates the cell/gel loading channel from the invasion chamber and allows passage of gel and invasive cells into the invasion chamber and where a substantially linear perfusion barrier separates the invasion chamber from the flow channel and defines a second side of the invasion chamber, opposite from the substantially linear invasion barrier, wherein the perfusion barrier is configured to retain the cell/gel mixture only within the invasion chamber and the cell/gel loading channel so that the cell/gel mixture does not enter the flow channel, wherein the flow channel is configured to provide a source of liquid media for feeding cells that are present in the cell/gel loading channel or the invasion chamber; and wherein the invasion chamber comprises a rectangular region, disposed between the invasion barrier and the perfusion barrier, that is small enough to fit within a diameter of the third well;

allowing cells in the cell/gel mixture to culture for an appropriate time; and observing the invasion chamber through the second well.

14. The method of claim 13, wherein a flow of media from the first well to the third well is driven by gravity flow, defined as a flow arising from a liquid height difference between the first well and the third well.

15. The method of claim 14, wherein a flow rate of media is about 20 µl/day.

16. The method of claim 13, wherein the substantially linear invasion barrier has a first set of channels having dimensions of about 50×8×8 µm in length, width and height or about 25-100 µm, 4-12 µm and 4-12 µm in length, width and height.

17. The method of claim 13, wherein the substantially linear perfusion barrier has a second set of channels having dimensions of about 2 µm or a minimum dimension of about 0.5-4 µm in height or width or both.

18. The method of claim 13, wherein the multi well plate comprises 48, 96, 192 or 384 wells.

19. The method of claim 13, wherein the first well, the second well and the third well are linearly arranged.

20. The method of claim 13, further comprising performing an invasion assay by enumerating a number of cells in the invasion chamber relative to a number of cells in the cell/gel loading channel at one or more points in time.

* * * * *